United States Patent [19]
Dondio et al.

[11] Patent Number: 5,922,887
[45] Date of Patent: Jul. 13, 1999

[54] DIARYLDIAMINE DERIVATIVES AND THEIR USE AS DELTA OPIOD (ANT)-AGONISTS

[75] Inventors: Giulio Dondio; Silvano Ronzoni, both of Milan, Italy

[73] Assignee: SmithKline Beecham SpA, Milan, Italy

[21] Appl. No.: 08/952,443

[22] PCT Filed: May 20, 1996

[86] PCT No.: PCT/EP96/02152

§ 371 Date: Nov. 18, 1997

§ 102(e) Date: Nov. 18, 1997

[87] PCT Pub. No.: WO96/36620

PCT Pub. Date: Nov. 21, 1996

[30] Foreign Application Priority Data

May 19, 1995 [IT] Italy ............................ MI95A1020

[51] Int. Cl.⁶ .................. C07D 207/00; C07D 207/08; C07C 211/00; C07C 45/90
[52] U.S. Cl. .................. 548/539; 514/423; 514/427; 514/619; 514/620; 514/648; 548/566; 564/167; 564/370; 564/433; 560/43
[58] Field of Search ...................... 564/370, 433, 564/167; 548/566, 539; 514/423, 427, 619, 620, 648

[56] References Cited

U.S. PATENT DOCUMENTS

| 2,739,981 | 3/1956 | Szabo et al. | 564/370 X |
| 2,739,984 | 3/1956 | Hafliger et al. | 564/370 |
| 2,889,328 | 6/1959 | Sherlock et al. | 564/370 X |
| 4,216,214 | 8/1980 | Subirana et al. | 424/244 |
| 4,217,452 | 8/1980 | Olivie | 544/246 |

FOREIGN PATENT DOCUMENTS

| 397 556 | 11/1990 | European Pat. Off. |  |
| 907646 | 10/1962 | United Kingdom. |  |
| 93-100 73 | 5/1993 | WIPO | 564/370 |
| 93/15062 | 8/1993 | WIPO . |  |

OTHER PUBLICATIONS

King, et al., "New Potential Chemotherapeutic Agents Part III", (1946), Journal of the Chemical Society, pp. 5–10 (1946).

Primary Examiner—Floyd D. Higel
Attorney, Agent, or Firm—Soma G. Simon; William T. King; Charles M. Kinzig

[57] ABSTRACT

A compound, or solvate or salt thereof, of formula (I)

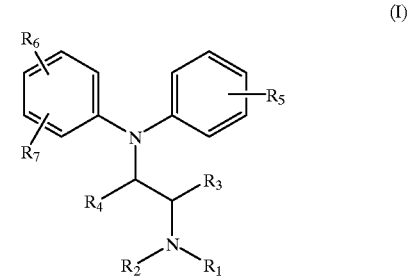

in which, $R_1$ and $R_2$, are, independently hydrogen, linear or branched $C_{1-6}$ alkyl, $C_{3-7}$ cycloalkyl, $C_{3-7}$ cycloalkenyl, or $C_{3-6}$ alkenyl, or together form a $C_{3-7}$ alkyl;

$R_3$ and $R_4$ are, independently, hydrogen, linear or branched $C_{1-6}$ alkyl, or $R_4$ is oxygen forming with the carbon atom to which is attached a C=O group;

$R_5$ is hydrogen, hydroxy, or $C_{1-3}$ alkoxy;

$R_6$ is halogen, $NH_2$ or a para or meta —COR-8 group, in which $R_8$ is $C_{1-8}$-alkyl, $C_{1-8}$-alkoxy or $NR_9R_{10}$, wherein $R_9$ and $R_{10}$, are, independently, hydrogen, straight or branched $C_{1-6}$ alkyl, $C_{3-7}$ cycloalkyl or phenyl; or $R_6$ is a para or meta group

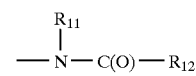

in which $R_{11}$ and $R_{12}$ are, independently, hydrogen or straight or branched $C_{1-6}$ and, $R_7$ is hydrogen, or straight or branched $C_{1-8}$ alkyl; is provided.

The present compound is useful as a delta opiod modulator.

10 Claims, No Drawings

DIARYLDIAMINE DERIVATIVES AND THEIR USE AS DELTA OPIOD (ANT)-AGONISTS

This application is a §371 of PCT/EP96/02152 filed May 20, 1996.

This invention is concerned with novel diaryldiamine derivatives, processes for their preparation, and their use in medicine.

The presence of at least three populations of opioid receptors (mu, delta and kappa) is now well established and documented and all three appear to be present in the central and peripheral nervous system of many species including man (Lord J. A. H. et al., Nature 1977, 267, 495).

Activation of all three opioid receptor subtypes can lead to antinociception in animal models. In particular, studies with peptidic delta agonists have indicated that activation of the delta receptor produces antinociception in rodents, primates and can induce clinical analgesia in man (D. E. Moulin et al. Pain, 1985, 23, 213). Evidences exist that suggest a lesser propensity of delta agonists to cause the usual side-effects associated with mu and kappa activation (Galligan et al, J. Pharm. Exp. Ther., 1984, 229, 641).

Substituted diaryldiamines as intermediates for the synthesis of dibenzodiazepines, useful as antihistaminic and antianaphylaptic agents, have been previously described [Brit. Pat. 907646, Dr. A. Wonder A. G.; Hunziker et al., Helv. Chim. Acta, 46,2337, (1963)].

European Patent 508,334 (Green Cross Corp.) discloses oxygen-substituted diaryldiamines which are said to be inhibitors of TPA-induced mouse ear edema WO 93/15062 (The Wellcome Foundation Limited) discloses diphenylpiperazine derivatives which are said to be agonists at all three opiate receptors.

We have now discovered a novel class of diaryldiamine derivatives which are potent and selective delta opioid agonists and antagonists which may therefore be of potential therapeutic utility as analgesics, immunosuppressants to prevent rejection in organ transplant and skin graft, anti-allergic and anti-inflammatory agents, brain cell protectant, agents for treating drug and alcohol abuse, gastritis, diarrhoea, cardiovascular and respiratory diseases, cough, mental illness, epilepsy and, more in general, agents for those pathological conditions which, customarily, can be treated with agonists and antagonists of the delta opioid receptor.

According to the present invention, there is provided a compound, or a solvate or salt thereof of formula (I):

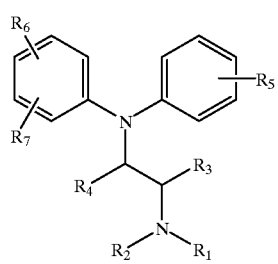

(I)

in which,

R$_1$ and R$_2$, which can be the same or different, are each hydrogen, linear or branched C$_{1-6}$ alkyl, C$_{3-7}$ cycloalkyl, C$_{3-7}$ cycloalkenyl, C$_{4-6}$ cycloalkylalkyl, C$_{3-6}$ alkenyl, C$_{3-5}$ alkenyl, aryl, aralkyl or furan-2 or 3-yl alkyl or may form together a C$_{3-7}$ alkyl ring which may be interrupted by an oxygen.

R$_3$ and R$_4$, which can be the same or different, are each hydrogen, linear or branched C$_{1-6}$ alkyl preferably methyl, or R$_4$ is oxygen forming with the carbon atom to which is attached a C=O group;

R$_5$ is hydrogen, hydroxy, C$_{1-3}$ alkoxy, preferably methoxy, mercapto, alkylthio, preferably methylthio;

R$_6$ is phenyl, para halogen, preferably bromine, para or meta NH$_2$ or a para or meta —C(Z)–R$_8$ group, in which Z is oxygen or sulphur, R$_8$ is C$_{1-8}$-alkyl, C$_{1-8}$-alkoxy or NR$_9$R$_{10}$, wherein R$_9$ and R$_{10}$, which may be the same or different, are hydrogen, straight or branched C$_{1-6}$ alkyl, C$_{3-7}$ cycloalkyl, C$_{4-6}$ cycloalkylalkyl, C$_{3-6}$ alkenyl, aryl, aralkyl, or together form a C$_4$ alkyl ring, or R$_6$ is a para or meta

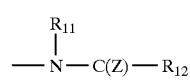

group
in which R$_{11}$ and R$_{12}$ which may be the same or different are hydrogen, straight or branched C$_{1-6}$ alkyl, C$_{3-7}$ cycloalkyl, C$_{4-6}$ cycloalkylalkyl, C$_{3-6}$ alkenyl, aryl, aralkyl or an optionally substituted heterocyclic ring and Z is as defined above; and, R$_7$ is hydrogen, straight or branched C$_{1-8}$ alkyl, halogen, preferably chlorine.

Examples of R$_1$ and R$_2$ are methyl, ethyl, cyclopropylmethyl, allyl or together with the N, pyrrolidino.

Examples of R$_3$ and R$_4$ are hydrogen, methyl, ethyl, i-propyl, or R$_4$ is =O.

Examples of R$_5$ are hydrogen, hydroxy, methoxy.

Examples of R$_6$ are COMe, CO—i—Pr, COOEt, CONH$_2$, CONH—n—Pr, CON(Me)Et, CON(Me)i—Pr, CONEt$_2$, CON(i—Pr)$_2$, CONEt(i—Pr), CON(—CH$_2$—)$_4$, NHCOi—Pr, NH$_2$, bromine, phenyl.

Examples of R$_7$ are hydrogen and methyl.

A first group of preferred compound of formula (I) are those in which each of R3 and R4 is hydrogen or C1–6 alkyl, preferably methyl or ethyl, and R$_1$, R$_2$, R$_5$, R$_6$ and R$_7$ are as defined above.

A second preferred group of compounds of formula (I) are those in which R$_5$ is an hydroxy or C1–3 alkoxy group, R$_1$, R$_2$, R$_6$ and R$_7$ are as defined above for formula (I) and each of R$_3$ and R$_4$ is hydrogen or C1–6 alkyl.

A particularly preferred group of compounds of formula (I) are those in which R$_6$ is a group —C(Z)—R$_8$ where R$_8$ is C$_{1-6}$ alkyl, OC$_{1-4}$ alkyl or NR$_9$R$_{10}$ where R$_9$ and R$_{10}$ are as defined above for formula (I), Z is oxygen, R$_1$, R$_2$ and R$_7$ are as defined above for formula (I), each of R$_3$ and R$_4$ is hydrogen or C1–6 alkyl, and R$_5$ is hydroxy or C1–3 alkoxy.

The compounds of formula (I) or their salts or solvates are preferably in pharmaceutically acceptable or substantially pure form. By pharmaceutically acceptable form is meant, inter alia, of a pharmaceutically acceptable level of purity excluding normal pharmaceutical additives such as diluents and carriers, and including no material considered toxic at normal dosage levels.

A substantially pure form will generally contain at least 50% (excluding normal pharmaceutical additives), preferably 75%, more preferably 90% and still more preferably 95% of the compound of formula (I) or its salt or solvate.

One preferred pharmaceutically acceptable form is the crystalline form, including such form in a pharmaceutical composition. In the case of salts and solvates the additional ionic and solvent moieties must also be non-toxic.

Examples of pharmaceutically acceptable salts of a compound of formula (I) include the acid addition salts with the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic.

ence of the NaH using DMF as solvent to obtain compounds of general formula (III). The ester group of these compounds may be reduced using $LiAlH_4$ in THF as solvent or, alternatively for compounds in which $R_6$ is a carbonyl containing group, using $NaBH_4$ in t-BuOH/MeOH as solvent to obtain compounds of general formula (IV). The alcohol derivatives are converted in their corresponding methanesulphonates and then treated with the appropriate amines obtaining compounds of general formula (I) along with their regioisomers in which $R_3=R_4$.

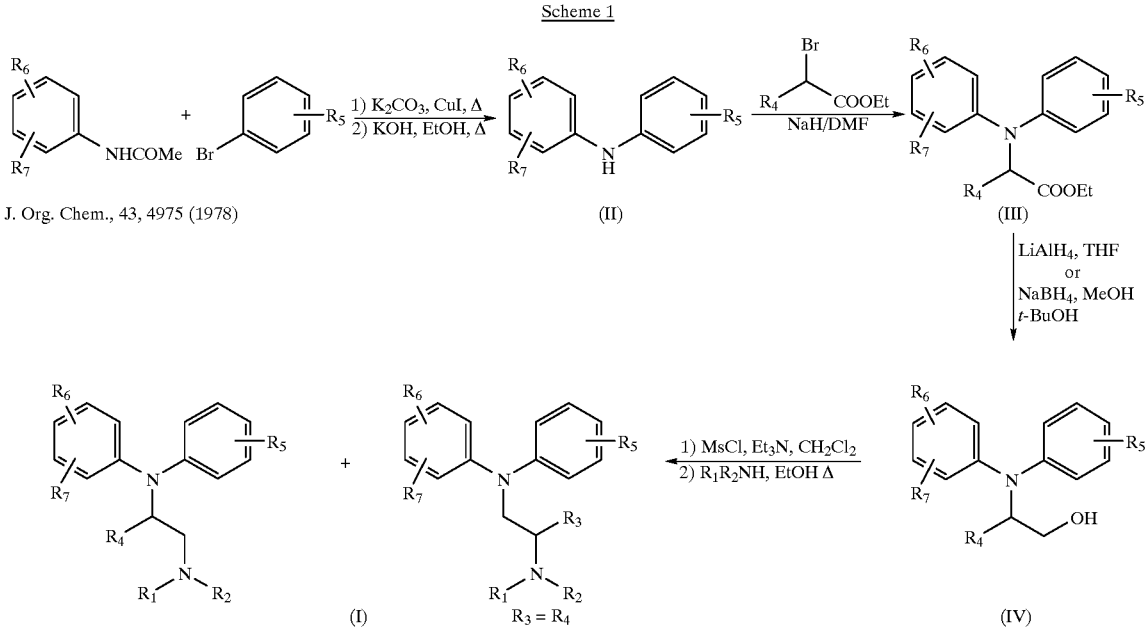

The compounds of formula (I) may exist in more than one stereoisomeric form, and the invention extends to all such forms as well as to their mixtures thereof, including racemates.

The present invention also provide a process for the preparation of a compound of formula (I). In general, these compounds may be prepared by the method illustrated in the following general reaction schemes, or by modification thereof, using readily available starting materials, reagents and conventional synthetic procedures. If a particular enantiomer of a compound of the present invention is desired, it may be synthesised starting from the desired enantiomer of the starting material and performing reactions not involving racemization processes or it may be prepared by chiral synthesis, or by derivation with a chiral auxiliary, where the resulting diastereomeric mixture is separated and the auxiliary group cleaved to provide the pure desired enantiomers. Alternatively, compounds of formula (I) can be separated into their enantiomers by forming diastereomeric salts with an appropriate optically active acid, followed by fractional crystallization resolution and subsequent recovery of the pure enantiomers.

Compounds of general formula (I) may be obtained following the procedure described in Scheme 1. Compounds of general formula (II) may be synthesised starting from substituted acetanilides and substituted bromobenzene derivatives in presence of CuI and $K_2CO_3$ as described in *J. Org. Chem*, 43, 4975 (1978). The bis-anilinic derivatives (II) may be alkylated using substituted α-bromo esters in pres- Alternatively, compounds of general formula (I) may be synthesised following the procedure described in Scheme 2. Esters of general formula (m), obtained as described in Scheme 1, may be treated with substituted amines under pressure. The corresponding amides may be reduced using $BH_3$—$Me_2S$ to obtain compounds of general formula (I) in which $R_3$ is H.

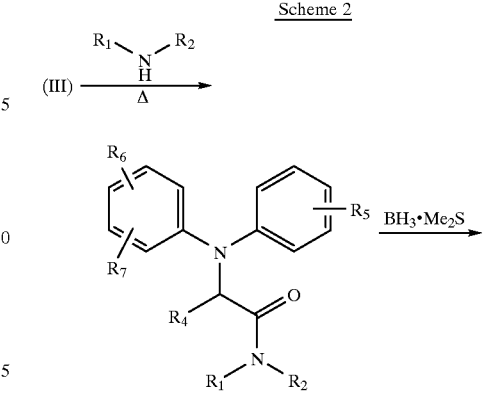

5
-continued

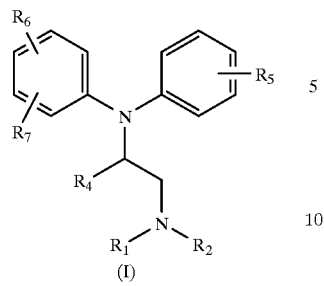

(I)

6
-continued

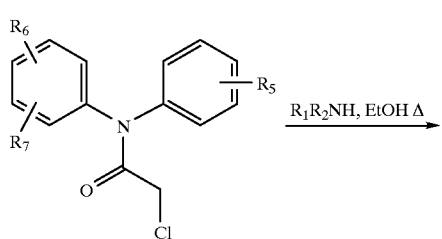

Compounds of general formula (I), in which $R_6$ is a group $COR_8$, where $R_8$ is as defined above, may be obtained starting from compounds of general formula (IIb) and (IIc), in turn obtained from compounds of formula (IIa) as outlined in Scheme 3. Amides (IIb) may be obtained treating the corresponding carboxylic acids (IIa) with the appropiates amines, using as condensing agents DCC/HOBT. Esters (IIc) are synthesised treating the compounds (IIa) with the corresponding alcohol in acidic media.

Scheme 3

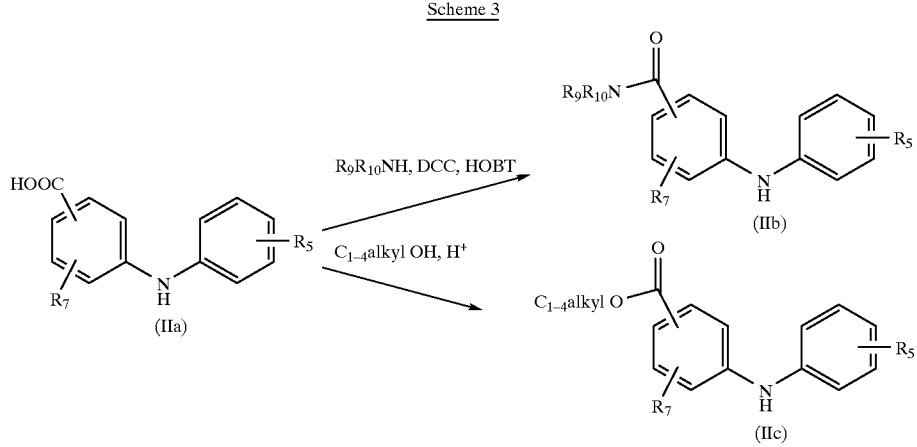

Compounds of general formula (I) where $R_4$ is =O may be prepared as described in Scheme 4. Compounds of general formula (II) are treated with chloroacetylchloride in boiling toluene. The resulting chloro derivatives are treated with the appropiate amines to obtain the final compounds of general formula (I).

Scheme 4

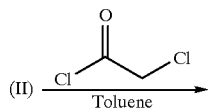

-continued

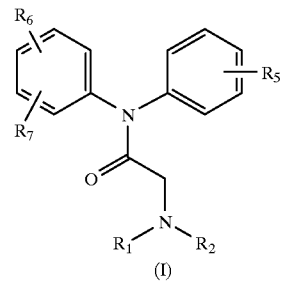

(I)

Compounds of general formula (I') in which $R_5$ is a MeO group, may be demethylated, for example, using $BBr_3$ in $CH_2Cl_2$ as solvent or alternatively, using $(CH_3)_3SiCl/NaI$ in boiling $CH_3CN$, to obtain other compounds of general formula (I) in which $R_5$ is OH. See Scheme 5.

Scheme 5

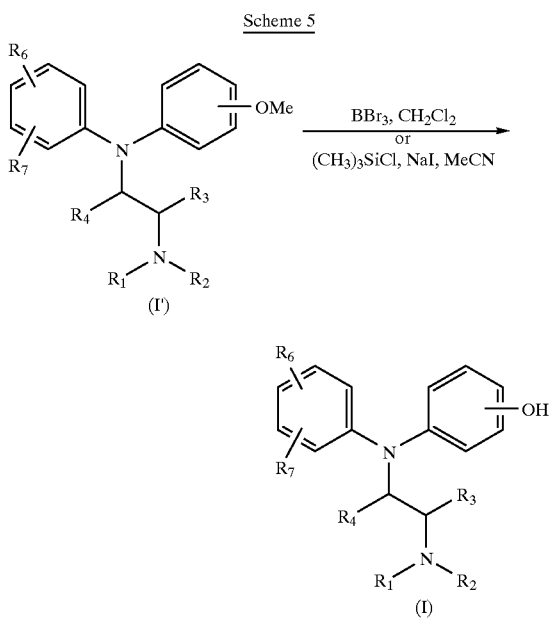

Compounds of general formula (I) may be obtained from phenotiazines of general formula (V) (described in EP0346238A1) removing the sulphur atom using $NICl_2/NaBH_4$. See Scheme 6.

Scheme 6

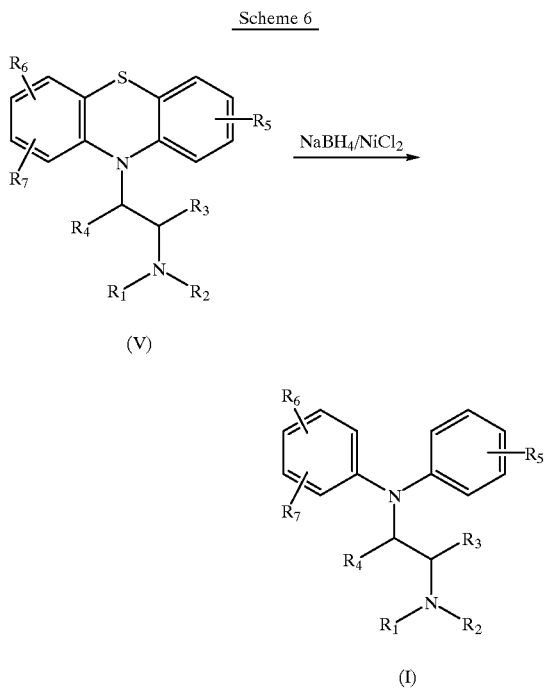

The compounds of formula (I) may be converted into their pharmaceutically acceptable salts by reaction with the appropriate organic or mineral acids.

Solvates of the compounds of formula (I) may be formed by crystallization or recrystallization from the appropriate solvent. For example, hydrates may be formed by crystallization or recrystallization from aqueous solutions, or solutions in organic solvents containing water.

Also salts or solvates of the compounds of formula (I) which are not pharmaceutically acceptable may be useful as intermediates in the production of pharmaceutically acceptable salts or solvates. Accordingly such salts or solvates also form part of this invention.

In general compounds of formula (I) acting as selective delta receptor ligands may be useful as analgesics, immunosuppressants to prevent rejection in organ transplant and skin graft, anti-allergic and anti-inflammatory agents, brain cell protectant, for the treatment of drug and alcohol abuse, to decrease gastric secretion, for the treatment of diarrhoea, cardiovascular and respiratory diseases, cough, mental illness, epileptic seizures and other neurologic disorders (herein after referred to as 'Conditions'). In particular, the activity of the compounds of formula (I) as delta agonists in standard tests indicates that they are of potential therapeutic utility as analgesic agents for the amelioration or elimination of pain.

Accordingly the present invention also provides a compound of formula (I), or a pharmaceutically acceptable salt or solvate thereof, for use as an active therapeutic substance.

The present invention also provides the use of a compound of formula (I), or a pharmaceutically acceptable salt or solvate thereof, in the manufacture of a medicament for the treatment of the Conditions.

Such a medicament, and a composition of this invention, may be prepared by admixture of a compound of the invention with an appropriate carrier. It may contain a diluent, binder, filler, disintegrant, flavouring agent, colouring agent, lubricant or preservative in conventional manner.

These conventional excipients may be employed for example as in the preparation of compositions of known agents for treating the conditions.

Preferably, a pharmaceutical composition of the invention is in unit dosage form and in a form adapted for use in the medical or veterinarial fields. For example, such preparations may be in a pack form accompanied by written or printed instructions for use as an agent in the treatment of the conditions.

The suitable dosage range for the compounds of the invention depends on the compound to be employed and on the condition of the patient. It will also depend, inter alia, upon the relation of potency to absorbability and the frequency and route of administration.

The compound or composition of the invention may be formulated for administration by any route, and is preferably in unit dosage form or in a form that a human patient may administer to himself in a single dosage. Advantageously, the composition is suitable for oral, rectal, topical, parenteral, intravenous or intramuscular administration. Preparations may be designed to give slow release of the active ingredient Compositions may, for example, be in the form of tablets, capsules, sachets, vials, powders, granules, lozenges, reconstitutable powders, or liquid preparations, for example solutions or suspensions, or suppositories.

The compositions, for example those suitable for oral administration, may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable setting agents such as sodium lauryl sulphate.

Solid compositions may be obtained by conventional methods of blending, filling, tabletting or the like. Repeated blending operations may be used to distribute the active agent throughout those compositions employing large quantities of fillers. When the composition is in the form of a tablet, powder, or lozenge, any carrier suitable for formulating solid pharmaceutical compositions may be used, examples being magnesium stearate, starch, glucose, lactose, sucrose, rice flour and chalk. Tablets may be coated according to methods well known in normal pharmaceutical practice, in particular with an enteric coating. The composition may also be in the form of an ingestible capsule, for example of gelatin containing the compound, if desired with a carrier or other excipients.

Compositions for oral administration as liquids may be in the form of, for example, emulsions, syrups, or elixirs, or may be presented as a dry product for reconstitution with water or other suitable vehicle before use. Such liquid compositions may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; aqueous or non-aqueous vehicles, which include edible oils, for example almond oil, fractionated coconut oil, oily esters, for example esters of glycerine, or propylene glycol, or ethyl alcohol, glycerine, water or normal saline; preservatives, for example methyl or propyl p-hydroxybenzoate or sorbic acid; and if desired conventional flavouring or colouring agents.

The compounds of this invention may also be administered by a non-oral route. In accordance with routine pharmaceutical procedure, the compositions may be formulated, for example for rectal administration as a suppository. They may also be formulated for presentation in an injectable form in an aqueous or non-aqueous solution, suspension or emulsion in a pharmaceutically acceptable liquid, e.g. sterile pyrogen-free water or a parenterally acceptable oil or a mixture of liquids. The liquid may contain bacteriostatic agents, anti-oxidants or other preservatives, buffers or solutes to render the solution isotonic with the blood, thickening agents, suspending agents or other pharmaceutically acceptable additives. Such forms will be presented in unit dose form such as ampoules or disposable injection devices or in multi-dose forms such as a bottle from which the appropriate dose may be withdrawn or a solid form or concentrate which can be used to prepare an injectable formulation.

The compounds of this invention may also be administered by inhalation, via the nasal or oral routes. Such administration can be carried out with a spray formulation comprising a compound of the invention and a suitable carrier, optionally suspended in, for example, a hydrocarbon propellant Preferred spray formulations comprise micronised compound particles in combination with a surfactant, solvent or a dispersing agent to prevent the sedimentation of suspended particles. Preferably, the compound particle size is from about 2 to 10 microns.

A further mode of administration of the compounds of the invention comprises transdermal delivery utilising a skin-patch formulation. A preferred formulation comprises a compound of the invention dispersed in a pressure sensitive adhesive which adheres to the skin, thereby permitting the compound to diffuse from the adhesive through the skin for delivery to the patient. For a constant rate of percutaneous absorption, pressure sensitive adhesives known in the art such as natural rubber or silicone can be used.

As mentioned above, the effective dose of compound depends on the particular compound employed, the condition of the patient and on the frequency and route of administration. A unit dose will generally contain from 20 to 1000 mg and preferably will contain from 30 to 500 mg, in particular 50, 100, 150, 200, 250, 300, 350, 400, 450, or 500 mg. The composition may be administered once or more times a day for example 2, 3 or 4 times daily, and the total daily dose for a 70 kg adult will normally be in the range 100 to 3000 mg. Alternatively the unit dose will contain from 2 to 20 mg of active ingredient and be administered in multiples, if desired, to give the preceding daily dose.

No unacceptable toxicological effects are expected with compounds of the invention when administered in accordance with the invention.

The present invention also provides a method for the treatment and/or prophylaxis of the Conditions in mammals, particularly humans, which comprises administering to the mammal in need of such treatment and/or prophylaxis an effective amount of a compound of formula (I) or a pharmaceutically acceptable salt or solvate thereof.

The activity of the compounds of the present invention as selective delta ligands is determined in radioligand binding assays as described below.

Mouse brain membranes were prepared as described by Kosterlitz (*Br. J. Pharmacol.*, 1981, 73, 939.). The binding of the preferential delta ligand [$^3$H]-[D-Ala$^2$, D-Leu$^5$]-enkephalin (DADLE) was evaluated at its $K_D$ concentration (1.3 nM) in presence of 40 nM of the unlabelled mu ligand [D-Ala$^2$, MePhe$^4$, Gly-ol$^5$]-enkephalin (DAMGO). The binding of the mu ligand [$^3$H]-DAMGO (*Eur. J. Pharmacol.*, 1989, 166, 213) and of the kappa ligand [$^3$H]-U69593 (*Excerpta Medica*, 1990, 211) were carried out at 0.5 nM. The non-specific binding was determined in presence of naloxone (10 $\mu$M) for all tritiated ligands. Binding data were expressed as percentage of inhibition and fitted the following equation: $f(x)=100 \cdot X/(IC_{50}+X)$ where X are cold drug concentration values. The $IC_{50}$ obtained were used to calculate the inhibitory constants ($K_i$) accordingly to the Cheng and Prusoff relation (*Biochenl. Pharmaco.*, 1973, 22, 3099).

The delta agonist/antagonist activity of the compounds of the present invention is determined in the mouse vas deferens (MVD) bioassay as described below.

Vasa deferentia were obtained from CD-1 mice and were suspended in a Mg$^{2+}$-free Krebs buffer at 37° C. The tissues were electrically stimulated with pulse trans having the following parameters: train duration 50 ms, stimulus duration 2 ms, frequency of stimuli 50 Hz, maximal voltage 60–70 V, train frequency 0.1 Hz. Concentration response curves for each compounds were constructed cumulatively. Linear regression analysis and $IC_{50}$ concentrations were evaluated according to Tallarida and Murray (*Manual of Pharmacological Calculations*, Springer Verlag N.Y., 1981).

The most potent compounds of the present invention showed affinities for the delta receptor ranging from 0.5 to 200 nM with delta selectivity ranging from 10 to 1500 times in respect to the other opioid receptor types. These compounds displayed also potent delta agonist or antagonist properties in the MVD preparation. Selective delta agonists (antagonised by the selective delta antagonist naltrindole) displayed $IC_{50}$s ranging from 1 to 500 nM. For example, the compound of Example 5 showed a $K_i\delta=3.9$ nM and in the MVD bioassay an $IC_{50}=7$ nM (30 nM of NTI caused a 10-fold shift of the dose-response curve); the compound of Example 9 showed a $K_i\delta=3.9$ nM, $K_i\mu/K_i\delta=148$ and $K_i\kappa/K_i\delta=153$.

Mouse abdominal constriction (MAC) (*Proc. Soc. Exp. Biol. Med.*, 1957, 95, 729), mouse tail-flick (MTF) (*J. Pharm. Exp. Ther.*, 1941, 22, 74) and mouse tail-flick warm water (MTF-WW) (*Life Sci.*, 1986, X, 1795) tests were adopted to evaluate the antinociceptive activity of the compounds of the present invention.

The following Preparations illustrate the preparation of intermediates, whereas the Procedures illustrate the preparation of compounds of the present invention. These compounds are summarised in the chemical table 4 and the analytical data are summarised in table 5.

PREPARATION 1

N,N-Diethyl-4-[N-(3-methoxyphenyl)amino]benzamide 3.7 g (2.3 mmol) of N-acetyl-m-anisidine, 10.6 g (41.4 mmol) of 4-bromo-N,N-diethylbenzamide and 0.42 g of CuI were heated to 1000° C.; 3 g (22.3 mmol) of $K_2CO_3$ were added and the resulting mixture was heated to 250° C. for 2 hours. The residue was dissolved in $CH_2Cl_2$ and washed with $H_2O$, the organic layer was dried over $Na_2SO_4$ and the solvent was removed in vacuo. The resulting residue was dissolved in 20 ml of absolute EtOH and refluxed for 2 h. The solvent was removed in vacuo, the residue was taken up in $H_2O$ and the aqueous layer extracted with AcOEt. The organic layer was dried over $Na_2SO_4$ and the solvent removed in vacuo. The resulting residue was purified by flash chromatography (AcOEt/Hexane 6:4), yielding 3 g of the title compound.

IR cm$^{-1}$(neat): 3300, 1595, 1535.

MS (EI) m/z: 297.6 (M-1)

Compounds of general formula (II) described in Table 1 were obtained following the same procedure.

PREPARATION 2

1-[4-[[-(3-Methoxyphenyl)]amino]benzoyl]pyrrolidine 2 g (8.2 mmol) of 4-[N-(3-methoxyphenyl)aminobenzoic acid, 2.2 g (16.4 mmol) of N-hydroxybenzotriazole and 1 ml (12.3 mmol) of pyrrolidine were dissolved in 40 ml of a 7:3 mixture of THF/CH$_3$CN, under a nitrogen atmosphere. The solution was cooled to 0° C. and 3.4 g (16.4 mmol) of dicyclohexylcarbodiimide dissolved in 20 ml of $CH_2Cl_2$ were added. The reaction mixture was allowed to warm to room temperature during 1 h., stirred an additional hour, then the precipitate was filtered off and the solvent was removed in vacuo. The residue was taken up with water and extracted with AcOEt, the organic layer was dried over $Na_2SO_4$ and the solvent removed in vacuo. The resulting crude mixture was purified by flash chromatography (AcOEt), yielding 2.4 g of the title compound.

IR cm$^{-1}$ (KBr): 3280, 1600, 1435;

MS (EI) m/z: 296.1.

N,N-diisopropyl-4-[N-(3-methoxyphenyl)amino]benzamide was obtained using the same procedure.

IR cm$^{-1}$ (KBr): 3280, 1600, 1340;

MS (EI) m/z: 326.1.

PREPARATION 3

(±)-N,N-Diethyl-4-[[N-(1-ethoxycarbonylethyl)-N-(3-methoxyphenyl)]amnolbenzanide 2 g (51.6 mmol) of a 60% mineral oil suspension of NaH were placed, under a nitrogen atmosphere, in 100 ml of DMF. The resulting suspension was cooled to 0° C. and 7.7 g (25.8 mmol) of N,N-diethyl-4-[N-(3-methoxyphenyl)amino]benzamide dissolved in 50 ml of DMF were added. After 1 h 8.4 ml (64.5 mmol) of ethyl 2-bromopropionate in 25 ml of DMF were added. The reaction mixture was allowed to warm to room temperature overnight, then $H_2O$ was added, the organic layer was collected, dried over Na2SO$_4$ and the solvent was removed in vacuo. The crude reaction mixture was purified by flash chromatography (AcOEt/hexane 6:4), yielding 3.5 g of the title compound.

IR cm$^{-1}$ (neat): 2980, 1740, 1610.

MS (EI) m/z: 398

TABLE 1

(II)

| NAME | R$_1$ | R$_2$ | IR cm$^{-1}$ (neat) | MS (EI) m/z |
|---|---|---|---|---|
| 4-Bromo-3'-methoxy diphenylamine | H | Br | 3380, 1580, 1490 | |
| 3'-Methoxy-4-phenyl diphehylamine | H | Ph | 3400, 1600, 1540 | 275.1 |
| 4-[N-(3-Methoxyphenyl)amino] benzoic acid | H | COOH' | 3380, 1660, 1590 | 243.0 |
| N,N-Diethyl-3-[N-(3-methoxyphenyl)amino] benzamide | CONEt$_2$ | H | 3280, 1600, 1580 | 298.0 |
| 3'-Methoxy-4-nitro diphenyldiamine | H | NO$_2$ | 3340, 1580, 1300 | 244.3 |

Compounds of general formula (II) may also be prepared according to the following procedure:

Compounds of general formula (III) described in Table 2, were obtained following the same procedure.

TABLE 2

(III)

| NAME | R | $R_1$ | $R_2$ | IR cm$^{-1}$ (neat) | MS (EI) m/z |
|---|---|---|---|---|---|
| (±)-Ethyl-2-[N-(4-bromophenyl)-N-(3-methoxyphenyl)]amino propionate | Me | H | Br | 2980, 1740, 1580 | 379 (M + 1) |
| Ethyl-N-(4-bromophenyl)-N-(3-methoxyphenyl)]amino acetate | H | H | Br | 1760, 1585, 1495 | |
| (±)-Ethyl-2-[N-(4-biphenylyl)-N-(3-methoxyphenyl)]amino propionate | Me | H | Ph | 1750, 1615, 1490 | 375.2 |
| N,N-Diethyl-4-[[N-ethoxycarbonylmethyl-N-(3-methoxyphenyl)]amino]benzamide | H | H | CONEt$_2$ | 1750, 1620, 1595 | 384.1 |
| (±)-N,N-Diethyl-4-[[N-(1-ethoxycarbonylpropyl)-N-(3-methoxyphenyl)]amino]benzamide | Et | H | CONEt$_2$ | 2980, 1740, 1620 | 412.2 |
| (±)-1-[4-[[N-(1-Ethoxycarbonylethyl)-N-(3-methoxyphenyl)[amino]benzoly]pyrrolidine | Me | H | CON(CH$_2$)$_4$ | 1755, 1615, 1590 | 396.0 |
| (±)-N,N-Diisopropyl-4-[[N-(1-ethoxycarbonylethyl)-N-(3-methoxyphenyl)]amino]benzamide | Me | H | CON(i-Pr)$_2$ | 2980, 1740, 1620 | 426.2 |
| (±)-N,N-diethyl-3-[[N-(1-ethoxycarbonylethyl)-N-(3-methoxyphenyl)]amino]benzamide | Me | CONEt$_2$ | H | 2980, 1740, 1635 | 398.1 |
| (±)-Ethyl-2-[N-(4-nitrophenyl)-N-(3-methoxyphenyl)]amino propionate | Me | H | NO$_2$ | 2980, 1740, 1590 | 344.1 |

PREPARATION 4

(±)-N,N-Diethyl-4-[[N-(1-hydroxyprop-2-yl)-N-(3-methoxyphenyl)]amino]benzamnide.

1.13 g (2.8 mmol) of (:)N,N-diethyl-4-([N-(1-ethoxycarbonylethyl)N-(3-methoxyphenyl)amino] benamide were dissolved, under a nitrogen atmosphere, in 14 ml of t-BuOH and 0.27 g (7 mmol) of NaBH$_4$ were added. The reaction mixture was heated to reflux and 2.5 ml of MeOH were added during 1 h. The solution was refluxed 2h, then H$_2$O was added, the solvent was removed in vacua, the residue was taken up in H$_2$)O and extracted with AcOEt. The organic layer was dried over Na2SO$_4$ and the solvent was removed in vacuo. The crude reaction mixture was purified by flash chromatography (AcOEt/hexane 9:1), yielding 0.5 g of the title compound.

IR cm$^{-1}$ (neat): 3350, 2990, 1600;

MS (EI) m/z: 356.1.

Compounds of general formula (IV) and described in Table 3 were obtained following the same procedure.

TABLE 3

(IV)

| NAME | R | $R_1$ | $R_2$ | IR | MS |
|---|---|---|---|---|---|
| (±)-2-[N-(4-Biphenylyl)-N-(3-methoxyphenyl)[aminopropanol | Me | H | p-Ph | 3380, 2980, 1600 | 333.1 |
| N,N-Diethyl-4-[[N-(2-hydroxyethyl)-N-3-methoxyphenyl)]amino]benzamide. | H | H | p-CONEt$_2$ | 3400, 2980, 1600 | 342.1 |

TABLE 3-continued (IV)

[structure: MeO-phenyl-N(R, CH2OH)-phenyl-R1,R2]

| NAME | R | R1 | R2 | IR | MS |
|---|---|---|---|---|---|
| (±)-N,N-Diethyl-4-[[N-(1-hydroxybut-2-yl)-N-(3-methoxyphenyl)]amino]benzamide. | Et | H | p-CONEt2 | 3400, 1595, 1280 | 370.1 |
| (±)-1-[4-[[N-(1-Hydroxyprop-2-yl)-N-3-methoxyphenyl)]amino]benzoyl]pyrrolidine | Me | H | p-CON(CH2)4 | 3380, 1590, 1430 | 354.0 |
| (±)-N,N-Diisopropyl-4-[[N-(1-hydroxyprop-2-yl)-N-(3-methoxyphenyl)]amino]benzamide. | Me | H | p-CON(i-Pr)2 | 3360, 1600, 1265 | 384.2 |
| (±)-N,N-Diethyl-3-[[N-(1-hydroxyprop-2-yl)-N-(3-methoxyphenyl)]amino]benzamide. | Me | p-CONEt2 | H | 3400, 1600, 1490 | 356.2 |

PREPARATION 5

(±)-Ethyl-2[-N-(4-aminophenyl)-N-(3-methoxyphenyl)]amino propionate 1.5 g (4.3 mmol) of (t)-ethyl-2-[N-(4-nitrophenyl)-N-(3-methoxyphenyl)]amino propionate were dissolved in 50 ml of abs.EtOH; 150 mg of 10% Pd/C were added and the resulting mixture was hydrogenated in a Parr apparatus at 40 psi for 2 h. The catalyst was filtered off and the solvent removed in vauo, yielding 1.2 g of the tithe product.

IR cm$^{-1}$ (neat): 3460, 3360, 1730;

MS (EI) m/z: 314.2.

Compounds of general formula (V) may be prepared according to the following procedure:

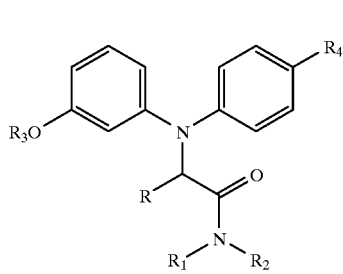

(V)

PREPARATION 6

(±)-1-[2-[[N-(4-bromophenyl)-N-(3-methoxyphenyl)]amino]propionyl]pyrrolidine 6.2 g (16.4 mmol) of (±)-ethyl-2-[N-(4-bromophenyl)-N-(3-methoxyphenyl)] aminopropionate and 100 ml of pyrrolidine were placed in a medium-pressure apparatus and heated to 200° C. overnight. The pyrrolidine was then removed in vacuao, the residue was taken up in CH$_2$Cl$_2$ and washed with 5% HCl. The organic layer was dried over Na$_2$SO$_4$ and the solvent was removed in vacuo, yielding 6 g of the title compound.

IR cm$^{-1}$ (neat): 2985, 1650, 1610;

MS (EI) m/z:402 (M−1).

1-[2-[[N-(4-bromophenyl)-N-(3-hydroxyphenyl)]amino]acetyl]pyrrolidine was obtained following the same procedure.

IR cm$^{-1}$ (KBr): 3180, 1630, 1590;

MS (EI) mlz: 374.1.

1-[2-[[N-(4-aminophenyl)-N-(3-methoxyphenyl)]amino]acetyl]pyrrolidine was obtained following the same procedure.

IR cm$^{-1}$ (KBr): 3440, 3340, 1630;

MS (EI) m/z: 339.1.

PREPARATION 7

N,N-Diethyl4-[[N-chloroacetyl-N-(3-methoxyphenyl))amino]benzamide 3.7 g (12.4 mmol) of N,N-diethyl-4-[N-(3-methoxyphenyl)amino]benzamide and 1.2 ml (14.9 mmol) of chloroacetylchloride were heated to reflux in 40 ml of toluene for 2 h under a nitrogen atmosphere. The solvent was removed in vacuo, the residue taken up with H$_2$O and extracted with AcOEt. The organic layer was dried over Na$_2$SO$_4$ and the solvent was removed in vacuo. The crude reaction mixture was purified by flash chromatography (AcOEt/hexane 8:2), yielding 2.9 g of the title compound.

IR cm$^{-1}$ (neat): 2980, 1695, 1635;

MS (EI) m/z: 374.

N,N-Diisopropyl-4-[[N-chloroacetyl-N-(3-methoxyphenyl))amino]benzamide was obtained following the same procedure.

IR cm$^{-1}$ (neat): 3280, 1690, 1620;

The compounds of the Examples described in Table 4, whose spectroscopic data are summarised in Table 5, were prepared by processes analogous to those described in Procedures A to I, which are fully described for some selected examples.

PROCEDURE A (±)-N,N-Diethyl-[[N-(3-methoxyphenyl)-N-(2-pyrrolidinyl-1-butyl)]amino]benzamide hydrochloride -Example 39-and (±)-N,N,-diethyl-4-[[N-(3-methoxyphenyl)-N-(1-pyrrolidinyl-2-butyl)] amino]benzade hydrochloride -Example 38

To a solution of 1.0 g (2.7 mmol) of (±)-N,N-diethyl-4-t[N-(1-hydroxybut-2-yl)N-(3-methocyphenyl)]amino] benzamide in 10 ml of $CH_2Cl_2$ were added, under a nitrogen atmosphere and at 10° C., 0.6 ml (4.3 mmol) of $Et_3N$ and 0.3 ml (4.3 mmol) of methanesulfonylchloride dissolved in 4 ml of $CH_2Cl_2$. After 90 min. the reaction mixture was poured in water, the layers were separated and the organic layer was washed with brine, dried over $Na_2SO_4$ and the solvent removed in vacuo. The residue was dissolved in 50 ml of toluene, 5 ml of pyrrolidine were added and the solution heated overnight at 90° C. The solvent was removed in vacuo, the residue brought to acidic pH with 5% HCl and the aqueous layer extracted with $Et_2O$, then brought to pH 14 with 15% NaOH and extracted with AcOEt. The organic layer was dried over $Na_2SO_4$ and the solvent removed in vacuo. The residue was purified by flash chromatography [(i—Pr)$_2$O/i—PrOH/conc. $NH_4OH$ 98:2:0.5] yielding, after acidification with $Et_2O$/HCl, 200 mg of the product showing the higher Rf, corresponding to (±)-N,N-diethyl-4-[[N-(3-methoxyphenyl)-N-(1-pyrrolidinyl-2-butyl)]amino] benzamide hydrochloride and 170 mg of the product showing the lower Rf, corresponding to (:t)-N,N-diethyl-4-[[N-(3-methoxyphenyl)-N-(2-pyrrolidinyl-1-butyl)]amino] benzamide hydrochloride.

PROCEDURE B (±)-N,N-Diethyl-4-[[N-(3-dimethylaminoprop-2-yl)-N-(3-methoxyphenyl)]amino]benzamide-Example 31-and (±)-N,N-diethyl-4-[[N (2-dimethylaninoprop-1yl).N-(3-methoxyphenyl)] amino]benzide -Example 30

To a solution of 2.0 g (5.6 mmol) of (+)-N,N-diethyl-4-[[N-(1-hydroxyprop-2-yl)-N-(3-methoxyphenyl)]amino] benzamide in 20 ml of $CH_2Cl_2$ were added, under a nitrogen atmosphere and at 10° C., 1.25 ml (9.0 mmol) of $Et_3N$ and 0.69 ml (9.0 mmol) of methanesulfonylchloride dissolved in 8 ml of $CH_2Cl_2$. After 90 min the reaction mixture was poured in water. The organic layer was washed with brine, dried over $Na_2SO_4$ and the solvent removed in vacuo. The residue was dissolved in 30 ml of a 33% ethanolic solution of dimethylamine, the reaction mixture was placed in a medium-pressure apparatus and heated overnight at 80° C. The solvent was removed in vacuo, the residue brought to acidic pH with 5% HCl and the aqueous phase extracted with $Et_2O$, then brought to pH 14 with 15% NaOH and extracted with AcOEt. The organic layer was dried over $Na_2SO_4$ and the solvent removed in vacuo. The crude reaction mixture was purified by flash chromatography ($CH_2Cl_2$/MeOH/conc.$NH_4OH$ 94.5:5:0.5), yielding 790 mg of the product showing the higher Rf, corresponding to (±)-N,N-diethyl-4-[[N-(3-dimethylaminoprop-2-yl)-N-(3-methoxyphenyl)]amino]benzamide, and 645 mg of the product showing the lower Rf, corresponding to (±)-N,N-diethyl-4-[[N-(2-dimethylaminoprop-1-yl)-N-(3-methoxyphenyl)] amino]benzamide.

PROCEDURE C -Example 3

(±)-N-(4-Bromophenyl).N-(3-methoxyphenyl)-α-methyl-1-pyrrolidinoethanamine citrate A solution of 2.6 g (6.4 mmol) of (±)-1-[2-[[N-(4-bromophenyl)-N-(3-methoxyphenyl)]amino]propionyl] pyrrolidine in 80 ml of dry THF was refluxed under a nitrogen atmosphere, then 4.2 ml (41.6 mmol) of a 10 M solution of $BH_3 \cdot Me_2S$ were added slowly. After 4 h. the solution was cooled to 0° C. and 15 ml of $H_2O$, 15 ml of 10% HCl and 15 ml of 37% HCl were added respectively. the reaction mixture was brought to reflux for 4 h then cooled and the volatiles removed in vacuo. The residue was taken up in water, brought to pH 14 with 40% NaOH and extracted with $Et_2O$. The organic layer was dried over $Na_2SO_4$ and the solvent removed in vacuo. The crude reaction mixture was purified by flash chromatography ($CH_2Cl_2$/MeOH/conc.$NH_4OH$ 98:2:0.4), yielding 1.5 g of the title compound as a free base. 150 mg of product were dissolved in MeOH, an equimolar amount of anhydrous citric acid was added, the solvent was removed in vacuo and the resulting solid triturated with $Et_2O$, yielding 100 mg of the title compound.

PROCEDURE D -Example 2

(±)-N-(4-Bromophenyl)-N (3-hydroxyphenyl)-α-methyl-1-pyrrolidinoethanamine hydrochloride 0.85ml (9 mmol) of boron tribromide were dissolved in 15 ml of dry $CHCl_3$ under a nitrogen atmosphere. 1.6 g (1.5 mmol) of (±)-N-(4-bromophenyl)-N-(3-methoxyphenyl-α-methyl-1-pyrrolidinoethanamine dissolved in 7 ml of dry $CHCl_3$ were added at room temperature. After 2 h. the solution was poured onto 15 g of crushed ice containing 1.5 ml of concd. $NH_4OH$ and stirred for 20 min. The layers were separated and the organic phase was dried over $Na_2SO_4$ and the solvent removed in vacuo. The crude reaction mixture was purified by flash chromatography ($CH_2Cl_2$/MeOH/conc.$NH_4OH$ 94.5:5:0.5). The resulting solid was dissolved in MeOH, the solution was brought to acidic pH with $Et_2O$/HCl and the solvent was removed in vacuo. The solid product obtained was triturated in $Et_2O$, yielding 365 mg of the title compound.

PROCEDURE E -Example 1

(−)-3-N-(3-pyrrolidinoprop-2-yl)phenylamino]-N-propylbenzamide hydrobromide

To a solution of 130 mg (0.33 mmol) of (+)-N-propyl-10-(3-pyrrolidinoprop-2-yl) phenothiazin-2-carboxamide (EP0346238A1) and 1.1 g (4.62 mmol) of $NiCl_2 \cdot 6H_2O$ in 16 ml of a mixture MeOH:THF:$H_2O$ 1:2:1 respectively, 524 mg (13.86 mmol) of $NaBH_4$ were added at room temperature. After 3h the reaction mixture was poured over a pad of celite, the solvent was removed in vacuo and the resulting residue was taken up in H₂0 and extracted with Ch₂Cl₂. The organic phase was dried over Na₂SO₄ and the solvent removed in vacuo. The crude reaction mixture was purified by flash chromatography (AcOEt/MeOH/conc.NH₄OH 95:5:0.5). The resulting solid was dissolved in acetone, the solution was brought to acidic ph with 24% HBr and the solvent was removed in vacuo. The resulting solid was triturated with (i-Pr)₂O, yielding 50 mg of the title compound.

$[\alpha]^{25}_D = -96$ (c=0.1,MeOH)

PROCEDURE F -Example 17

N,N-Diethyl.4.[[N.(dimethylaminoacetyl)-N-(3-methoxyphenyl)]amino]benzamide citrate A solution of 1.4 g (3.9 mmol) of N,N-diethyl-4-[[N-chloroacetyl-N-(3-methoxyphenyl)[amino]benzamide in 30 ml of a 33% ethanolic solution of dimethylanine was placed in a medium-pressure apparatus and heated overnight at 80° C. The solvent was removed in vacuo, the residue brought to acidic pH with 5% HCl and the aqueous phase extracted with Et₂O, then brought to pH 14 with 15% NaOH and extracted with AcOEt. The organic layer was dried over Na2SO₄ and the solvent removed in vacuo. The crude reaction mixture was purified by flash chromatography (CH₂Cl₂/MeOH/conc.NH₄OH 90:7:0.7), yielding 1.7 g of the title compound as a free base. 50 mg of product were dissolved in MeOH, an equimolar amount of anhydrous citric acid was added and the solvent was removed in vacuo. The resulting solid was triturated with Et₂O, yielding 30 mg of the title compound.

PROCEDURE G -Example 43

(±)-N-[[4-[N-(3-Methoxyphenyl)-N-[l-methyl-2 (1-pyrrolidinyl)ethyl]]amino]phenyl]-2-methylpropanamide To a solution of 0.98 g (3.0 mmol) of (±)-N-(4-aminophenyl)-N-(3-methoxyphenyl)_α-methy-1-pyrrolidinoethanamine in 25 ml of dry CH₂Cl₂, 1g (7.5 mmol) of K₂CO₃ was added. The reaction mixture was cooled to 0° C. and, under a nitrogen atmosphere, 0.8 g (7.5 mmol) of isobutyryl chloride dissolved in 10 ml of dry CH₂Cl₂ were added dropwise. After 15 h. at room temperature, water was added, the phases were separated and the organic phase dried over NASO₄ and the solvent removed in uacuo. The resulting residue was purified by flash chromatography (CH₂Cl₂/MeOH/conc.NH₄OH 94.5:5:0.5), yielding 1.0 g of the title compound.

PROCEDURE H

(−)-N,N-Diethyl-4-([N-(3-dimethylaminoprop-2-yl)-N-(3-hydroxyphenyl)]]amino]benzamide trifluoroacetate-Example 45-and (+)-N,N-Diethyl-4-[[N-(3-dimethylaminoprop-2-yl)-N-(3-hydroxyphenyl)]amino]benzanide trifluoroacetat -Example 46

The corresponding racemate was resolved by performing HPLC on chiral stationary phase Chiradex (Merk). Column: Lichrocart 25021 mm; eluent:

KH₂PO₄ (75 mM), TEA (0.2%), pH=4/MeCN=80/20

PROCEDURE I-Example 55

N,N-Diethyl-4-[[N-(diethylaminoacetyl)-N-(3-hydroxyphenyl)]amino]beuzamide Hydrochloride To a solution of 2 g (5.6 mmol) of N,N-diethyl-4-[[N-chloroacetyl-N-(3-methoxyphenyl)]amino]benzamide in 20 ml of toluene, 2.7 ml (25.8 mmol) of diethylamine were added and the resulting solution was heated to 60° C. for 15 h. The solvent was removed in vacuo, the residue was taken up in water and extracted with CH₂Cl₂, then the organic phase was dried over Na₂SO₄ and the solvent removed in vacuo. The resulting residue was purified by flash chromatography (CH₂Cl₂/MeOH/conc.NH₄OH 94.5:5:0.5), yielding 1.9 g of the title compound.

TABLE 4

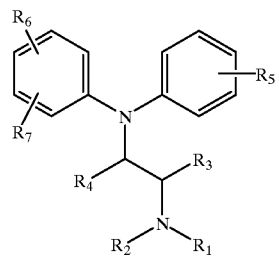

| Example | Procedure | Name | R1 | R2 | R3 | R4 | R5 | R6 | R7 | optical rot. |
|---|---|---|---|---|---|---|---|---|---|---|
| 1 | E | (−)-3-[N-(3-pyrrolidinoprop-2-yl)phenylamino]-N-propylbenzamide HBr | —(CH2)4— | | H | Me | H | m-CONH-nPr | H | (−) |
| 2 | D | (±)-N-(4-bromophenyl)-N-(3-hydroxyphenyl)-α-methyl-1-pyrrolidinoethanamine HCl | —(CH2)4— | | H | Me | OH | p-Br | H | (±) |
| 3 | C | (±)-N-(4-bromophenyl)-N-(3-methoxyphenyl)-α-methyl-1-pyrrolidinoetanamine citrate | —(CH2)4— | | H | Me | OMe | p-Br | H | (±) |
| 4 | A | (±)-N,N-diethyl-4-[[N-(3-methoxyphenyl)-N-(3-pyrrolidinoprop-2-yl)]amino]benzamide citrate | —(CH2)4— | | H | Me | OMe | p-CONEt2 | H | (±) |

TABLE 4-continued

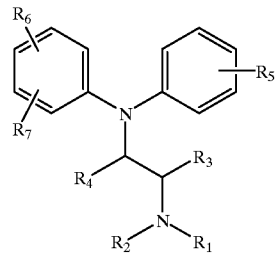

| Example | Procedure | Name | R1 | R2 | R3 | R4 | R5 | R6 | R7 | optical rot. |
|---|---|---|---|---|---|---|---|---|---|---|
| 5 | D | (±)-N,N-diethyl-4-[[N-(3-hydroxyphenyl)-N-(3-pyrrolidinoprop-2-yl)]amino]benzamide citrate | —(CH2)4— | | H | Me | OH | p-CONEt2 | H | (±) |
| 6 | C | N-(4-bromophenyl)-N-(3-hydroxyphenyl)-1-pyrrolidinoethanamine | —(CH2)4— | | H | H | OH | p-Br | H | |
| 7 | D | N,N-diethyl-4-[[N-(2-dimethylaminoethyl)-N-(3-hydroxyphenyl)]amino]benzamdie citrate | Me | Me | H | H | OH | p-CONEt2 | H | |
| 8 | D | (±)-N,N-diethyl-4-[[N-(2-dimethylaminoprop-1-yl)-N-(3-hydroxyphenyl)]amino]benzamide citrate | Me | Me | Me | H | OH | p-CONEt2 | H | (±) |
| 9 | D | (±)-N,N-diethyl-4-[[N-(3-dimethylaminoprop-2-yl)-N-(3-hydroxyphenyl)]amino]benzamide oxalate | Me | Me | H | Me | OH | p-CONEt2 | H | (±) |
| 10 | D | N,N-diethyl-4-[[N-(3-hydroxyphenyl)-N-(2-pyrrolidinoethyl)]amino]benzamide cirtate | —(CH2)4— | | H | H | OH | p-CONEt2 | H | |
| 11 | A | N,N-diethyl-4-[[N-(3-methoxyphenyl)-N-(2-pyrrolidinoethyl)]amino]benzamide oxalate | —(CH2)4— | | H | H | OMe | p-CONEt2 | H | |
| 12 | B | N,N-diethyl-4-[[N-(2-dimethylaminoethyl)-N-(3-methoxyphenyl)]amino]benzamide citrate | Me | Me | H | H | OMe | p-CONEt2 | H | |
| 13 | D | (±)-$N^2$-(4-biphenylyl)-$N^1,N^1$-dimethyl-$N^2$-(3-hydroxyphenyl)-1,2-propandiamine citrate | Me | Me | H | Me | OH | p-Ph | H | (±) |
| 14 | D | (±)-$N^1$-(4-biphenylyl)-$N^2,N^2$-dimethyl-$N^1$-(3-hydroxyphenyl)-1,2-propandiamine citrate | Me | Me | Me | H | OH | p-Ph | H | (±) |
| 15 | B | (±)-$N^2$-(4-biphenylyl)-$N^1,N^1$-dimethyl-$N^2$-(3-methoxyphenyl)-1,2-propandiammne citrate | Me | Me | H | Me | OMe | p-Ph | H | (±) |
| 16 | B | (±)-$N^1$-(4-biphenylyl)-$N^2,N^2$-dimethyl-$N^1$-(3-methoxyphenyl)-1,2-propandiamine citrate | Me | Me | Me | H | OMe | p-Ph | H | (±) |
| 17 | F | N,N-diethyl-4-[[N-(dimethylaminoacetyl)-N-(3-methoxyphenyl)]amino]benzamide citrate | Me | Me | H | C=O | OMe | p-CONEt2 | H | (±) |
| 18 | B | (±)-1-[4-[[N-(3-dimethylaminoprop-2-yl)-N-(3-methoxyphenyl)]amino]benzoyl]pyrrolidine citrate | Me | Me | H | Me | OMe | p-CON(CH2)4 | H | (±) |
| 19 | B | (±)-1-[4-[[N-(2-dimethylaminoprop-1-yl)-N-(3-methoxyphenyl)]amino]benzoyl]pyrrolidine citrate | Me | Me | Me | H | OMe | p-CON(CH2)4 | H | (±) |
| 20 | D | (±)-1-[4-[[N-(3-dimethylaminoprop-2-yl)-N-(3-hydroxyphenyl)]amino]benzoly]pyrrolidine citrate | Me | Me | H | Me | OH | p-CON(CH2)4 | H | (±) |
| 21 | D | (±)-1-[4-[[N-(2-dimethylaminoprop-1-yl)-N-3-hydroxyphenyl)]amino]benzoyl]pyrrolidina citrate | Me | Me | Me | H | OH | p-CON(CH2)4 | H | (±) |
| 22 | D | (±)-N,N-diethyl-3-[[N-(dimethylaminoprop-2-yl)-N-(3-hydroxyphenyl)]amino]benzamide citrate | Me | Me | H | Me | OH | m-CONEt2 | H | (±) |
| 23 | D | (±)-N,N-diethyl-3-[[N-(2-dimethylaminoprop-1-yl)-N-(3-hydroxyphenyl)]amino]benzamide citrate | Me | Me | Me | H | OH | m-CONEt2 | H | (±) |
| 24 | D | (±)-N,N-diisopropyl-4-[[N-(3-dimethylaminoprop-2-yl)-N-(3-hydroxyphenyl)]amino]benzamide citrate | Me | Me | H | Me | OH | p-CON(i-Pr)2 | H | (±) |
| 25 | D | (±)-N,N-diisopropyl-4-[[N-(2-dimethylaminoprop-1-yl)-N-(3-hydroxyphenyl)]amino]benzamide citrate | Me | Me | Me | H | OH | p-CON(i-Pr)2 | H | (±) |
| 26 | D | (±)-N,N-diethyl-3-[[N-(3-hydroxyphenyl)-N-(3-pyrrolidinoprop-2-yl)]amino benzamide citrate | —(CH2)4— | | H | Me | OH | m-CONEt2 | H | (±) |
| 27 | D | (±)-N,N-diethyl-3-[[N-(3-hydroxyphenyl)-N-(2-pyrrolidinoprop-1-yl)]amino]benzamide citrate | —(CH2)4— | | Me | H | OH | m-CONEt2 | H | (±) |
| 28 | D | (±)-N,N-diethyl-4-[[N-(3-hydroxyphenyl)-N-(1-pyrrolidinyl-2-butyl)amino]benzamide HCl | —(CH2)4— | | H | Et | OH | p-CONEt2 | H | (±) |
| 29 | D | (±)-N,N-diethyl-4-[[N-(3-hydroxyphenyl)-N-(2-pyrrolidinyl-1-butyl)]amino]benzamide HCl | —(CH2)4— | | Et | H | OH | p-CONEt2 | H | (±) |
| 30 | B | (±)-N,N-diethyl-4-[[N-(2-dimethylaminoprop-1-yl)-N-(3-methoxyphenyl)]amino]benzamide | Me | Me | Me | H | OMe | p-CONEt2 | H | (±) |
| 31 | B | (±)-N,N-diethyl-4-[[N-(3-dimethylaminoprop-2-yl)-N-(3-methoxyphenyl)]amino]benzamide | Me | Me | H | Me | OMe | p-CONEt2 | H | (±) |
| 32 | B | (±)-N,N-diethyl-3-[[N-(3-dimethylaminoprop-2-yl)-N-(3-methoxyphenyl)]amino]benzamide | Me | Me | H | Me | OMe | m-CONEt2 | H | (±) |
| 33 | B | (±)-N,N-diethyl-3-[[N-(2-dimethylaminoprop-1-yl)-N-(3-methoxyphenyl)]amino]benzamide | Me | Me | Me | H | OMe | m-CONEt2 | H | (±) |
| 34 | B | (±)-N,N-diisopropyl-4-[[N-(3-dimethylaminoprop-2-yl)-N-(3-methoxyphenyl)]amino]benzamide | Me | Me | H | Me | OMe | p-CON(i-Pr)2 | H | (±) |
| 35 | B | (±)-N,N-diisopropyl-4-[[N-(2-dimethylaminoprop-1-yl)-N-(3-methoxyphenyl)[amino]benzamide | Me | Me | Me | H | OMe | p-CON(i-Pr)2 | H | (±) |

TABLE 4-continued

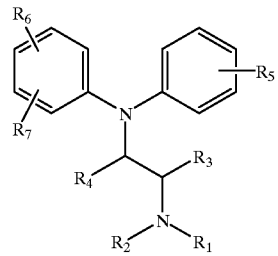

| Example | Procedure | Name | R1 | R2 | R3 | R4 | R5 | R6 | R7 | optical rot. |
|---|---|---|---|---|---|---|---|---|---|---|
| 36 | A | (±)-N,N-diethyl-3-[[N-(3-methoxyphenyl)-N-(3-pyrrolidinoprop-2-yl)]amino]benzamide | —(CH2)4— | | H | Me | OMe | m-CONEt2 | H | (±) |
| 37 | A | (±)-N,N-diethyl-3-[[N-(3-methoxyphenyl)-N-(2-pyrrolidinoprop-1-yl)]amino]benzamide | —(CH2)4— | | Me | H | OMe | m-CONEt2 | H | (±) |
| 38 | A | (±)-N,N-diethyl-4-[[N-(3-methoxyphenyl)-N-(1-pyrrolidinyl-2-butyl)]amino]benzamide HCl | —(CH2)4— | | H | Et | OMe | p-CONEt2 | H | (±) |
| 39 | A | (±)-N,N-diethyl-4-[[N-(3-methoxyphenyl)-N-(2-pyrrolidinyl-1-butyl)]amino]benzamide HCl | —(CH2)4— | | Et | H | OMe | p-CONEt2 | H | (±) |
| 40 | D | (±)-4-[N-[1-(N-allyl-N-methyl)amino-2-propyl]-N-(3-hydroxyphenyl)amino]-N,N-diethylbenzamide HCl | Me | Allyl | H | Me | OH | p-CONEt2 | H | (±) |
| 41 | D | (±)-4-[N-[2-(N-allyl-N-methyl)amino-1-propyl]-N-(3-hydroxyphenyl)amino]-N,N-diethylbenzamide HCl | Me | Allyl | Me | H | OH | p-CONEt2 | H | (±) |
| 42 | D | N,N-diethyl-4-[[N-(dimethylaminoacetyl)-N-3-hydroxyphenyl)]amino]benzamide HCl | Me | Me | H | C=O | OH | p-CONEt2 | H | |
| 43 | G | (±)-N-[[4-[N-(3-methoxyphenyl)-N-[1-methyl-2-(1-pyrrolidinyl)ethyl]]amino]phenyl]-2-methylpropanamide | —(CH2)4— | | H | Me | OMe | p-NHCOi-Pr | H | (±) |
| 44 | D | (±)-N-[[4-[N-(3-hydroxyphenyl)-N-[1-methyl-2-(1-pyrrolidinyl)ethyl]]amino]phenyl]-2-methylpropanamide citrate | —(CH2)4— | | H | Me | OH | p-NHCOi-Pr | H | (±) |
| 45 | H | (−)-N,N-diethyl-4-[[N-(3-dimethylaminoprop-2-yl)-N-(3-hydroxyphenyl)]amino]benzamide trifluoroacetate | Me | Me | H | Me | OH | p-CONEt2 | H | $[a]_D^{20}$ = −68.1; c = 0.1 MeOH |
| 46 | H | (+)-N,N-diethyl-4-[[N-(3-dimethylaminoprop-2-yl)-N-(3-hydroxyphenyl)]amino]benazmide trifluoroacetate | Me | Me | H | Me | OH | p-CONEt2 | H | $[a]_D^{20}$ = +60.5; c = 0.1 MeOH |
| 47 | D | N,N-diethyl-4-[[N-(diethylaminoacetyl)-N-(3-hydroxyphenyl)]amino]benzamide HCl | Et | Et | H | C=O | OH | p-CONEt2 | H | |
| 48 | D | N,N-diethyl-4-[[N-(3-hydroxyphenyl)-N-(pyrrolidin-1-ylacetyl)]amino]benzamide HCl | —(CH2)4— | | H | C=O | OH | p-CONEt2 | H | |
| 49 | D | N,N-diisopropyl-4-[[N-(dimethylaminoacetyl)-N-(3-hydroxyphenyl)]amino]benzamide | Me | Me | H | C=O | OH | p-CON(i-Pr)2 | H | |
| 50 | D | 4-[[N-[(N-allyl-N-methyl)amino]acetyl]-N-(3-hydroxyphenyl)]amino]-N,N-diethylbenzamide HCl | Me | Allyl | H | C=O | OH | p-CONEt2 | H | |
| 51 | D | N,N-diethyl-4-[[N-(3-hydroxyphenyl)-N-(methylaminoacetyl)]amino]benzamide HCl | H | Me | H | C=O | OH | p-CONEt2 | H | |
| 52 | D | N,N-diisopropyl-4-[[N-aminoacetyl-N-(3-hydroxyphenyl)]amino]benzamide | H | H | H | C=O | OH | p-CON(i-Pr)2 | H | |
| 53 | A | (±)-4-[N-[1-(N-allyl-N-methyl)amino-2-propyl]-N-(3-methoxyphenyl)amino]-N,N-diethylbenzamide | Me | Allyl | H | Me | OMe | p-CONEt2 | H | (±) |
| 54 | A | (±)-4-[N-[2-(N-allyl-N-methyl)amino-1-propyl]-N-(3-methoxyphenyl)amino]-N,N-diethylbenzamide | Me | Allyl | Me | H | OMe | p-CONEt2 | H | (±) |
| 55 | I | N,N-diethyl-4-[[N-(diethylaminoacetyl)-N-(3-methoxyphenyl)]amino]benzamide | Et | Et | H | C=O | OMe | p-CONEt2 | H | |
| 56 | I | N,N-diethyl-4-[[N-(3-methoxyphenyl)-N-(pyrrolidin-1-ylacetyl)]amino]benzamide | —(CH2)4— | | H | C=O | OMe | p-CONEt2 | H | |
| 57 | F | N,N-diisopropyl-4-[[N-(dimethylaminoacetyl)-N-(3-methoxyphenyl)]amino]benzamide | Me | Me | H | C=O | OMe | p-CON(i-Pr)2 | H | |
| 58 | I | 4-[[N-[(N-allyl-N-methyl)amino]acetyl]-N-(3-methoxyphenyl)]amino]-N,N-diethylbenzamide | Me | Allyl | H | C=O | OMe | p-CONEt2 | H | |
| 59 | F | N,N-diethyl-4-[[N-(3-methoxyphenyl)-N-(methylaminoacetyl)]amino]benzamide | H | Me | H | C=O | OMe | p-CONEt2 | H | |
| 60 | F | N,N-diisopropyl-4-[[N-aminoacetyl-N-(3-methoxyphenyl)]amino]benzamide | H | H | H | C=O | OMe | p-CON(i-Pr)2 | H | |
| 61 | C | (±)-N-(4-aminophenyl)-N-(3-methoxyphenyl)-α-methyl-1-pyrrolidionetanamine | —(CH2)4— | | H | Me | OMe | p-NH2 | H | (±) |

TABLE 5

| Ex. | NMR | MS | IR cm$^{-1}$ (KBr) |
|---|---|---|---|
| 1 | (CDCl3): 11.40(s br, 1H); 8.00(s br, 1H); 7.60(d, 1H); 7.37(dd, 2H); 7.25(dd, 1H); 7.18(dd, 1H); 7.08(d, 2H); 6.89(d br, 1H); 5.25(m, 1H); 4.00–3.80(m, 2H); 3.60–3.40(m, 2H); 3.49(dt, 2H); 3.30–3.20(m, 1H); 2.30–2.00(m, 4H); 1.77(ddq, 2H); 1.41(d, 3H); 1.00(t, 3H). | 365 (M+.); 281 EI; source 200 C; 70 V; 200 uA | 3420, 2960, 1640. |
| 2 | (CDCl3): 10.58(s br, 1H); 8.30(s br, 1H); 7.36(d, 2H); 7.11(dd, 1H); 6.85(d, 2H); 6.70(s br, 1H); 6.63(d, 1H); 6.36(d, 1H); 4.84(ddq, 1H); 4.00–3.70(m, 2H); 3.36(dd, 1H); 3.11(dd, 1H); 3.00–2.70(m, 2H); 2.30–1.90(m, 4H); 1.40(d, 3H). | 374–376 (M+.); 290–292, 84 EI; source 200 C; 70 V; 200 uA | 2980, 1585, 1490. |
| 3 | (DMSO): 11.00(s br, 4H); 7.41(d, 2H); 7.27(dd, 1H); 6.78(d, 2H); 6.72(d, 1H); 6.52(d, 1H); 6.50(s, 1H); 4.35(ddq, 1H); 3.72(s, 3H); 3.40–2.80(m, 6H); 2.60(ABq, 4H); 1.80(s br, 4H); 1.10(d, 3H). | 388–390 (M+.); 304–306; 84 EI; source 200 C; 70 V; 200 uA | 3440, 1730, 1580. |
| 4 | (DMSO): 10.80(s br, 4H); 7.33(dd, 1H); 7.23(d, 2H); 6.82(d, 1H); 6.74(d, 2H); 6.63(d, 1H); 6.62(s, 1H); 4.50(ddq, 1H); 3.75(s, 3H); 3.30(q br, 4H); 3.10–2.70(m, 6H); 2.60(ABq, 4H); 1.82(s br, 4H); 1.15(d, 3H); 1.10(t, 6H). | 409 (M+.); 325; 84 EI; source 200 C; 70 V; 200 uA | 2960, 1610, 1430 (free base). |
| 5 | (DMSO): 10.80(s br, 4H); 9.45(s br, 1H); 7.22(d, 2H); 7.21(dd, 1H); 6.73(d, 2H); 6.66(dd, 1H); 6.52(d, 1H); 6.46(dd, 1H); 4.47(ddq, 1H); 3.32(q br, 4H); 3.10–2.80(m, 6H); 2.60(ABq, 4H); 1.84(s br, 4H); 1.16(d, 3H); 1.10(t, 3H). | 395 (M+.); 311; 211; 84 EI; source 200 C; 70 V; 200 uA | 2980, 1730, 1600. |
| 6 | (DMSO): 9.30(s, 1H); 7.36(d, 2H); 7.09(dd, 1H); 6.86(d, 1H); 6.47(d, 1H); 6.45(s, 1H); 6.42(d, 1H); 3.72(t, 2H); 2.60(t, 2H); 2.44(m, 4H); 1.65(m, 4H). | 360–362 (M+.); 276–278; 84 EI; source 200 C; 70 V; 200 uA | 1620, 1570, 1485. |
| 7 | (DMSO): 11.00(s br, 4H); 9.45(s br, 1H); 7.24(d, 2H); 7.17(dd, 1H); 6.88(d, 2H); 6.58(d, 1H); 6.54(d, 1H); 6.52(s, 1H); 3.90(t, 2H); 3.32(q br, 4H); 2.92(t, 2H); 2.59(ABq, 4H); 2.55(s, 6H); 1.10(t, 6H). | 355 (M+.); 297; 197; 58; EI; source 200 C; 70 V; 200 uA | 3420, 1730, 1600. |
| 8 | (DMSO): 11.00(s br, 4H); 9.45(s br, 1H); 7.25(d, 2H); 7.17(dd, 1H); 6.90(d, 2H); 6.60(d, 1H); 6.55(d, 1H); 6.50(s, 1H); 3.92(dd, 1H); 3.72(dd, 1H); 3.40–3.20(m, 5H); 2.60(ABq, 4H); 1.10(d, 3H); 1.09(t, 3H). | 369 (M+.); 298; 72 EI; source 200 C; 70 V; 200 uA | 3400, 1730, 1600. |
| 9 | (DMSO): 7.20(d, 2H); 7.20(dd, 1H); 6.70(d, 2H); 6.65(d, 1H); 6.51(d, 1H); 6.44(s, 1H); 4.55(ddq, 1H); 3.50(dd, 1H); 3.40(dd, 1H); 3.30(q br, 4H); 2.60(s, 6H); 1.01(d, 3H); 1.06(t, 3H). | 369 (M+.); 311; 211; 58 EI; source 200 C; 70 V; 200 uA | 3200, 1600, 1450. (free base). |
| 10 | (DMSO): 11.00(s br, 4H); 9.45(s br, 1H); 7.25(d, 2H); 7.15(dd, 1H); 6.85(d, 2H); 6.60(d, 1H); 6.55(d, 1H); 6.50(s, 1H); 3.95(t, 2H); 3.40–3.00(m, 10H); 2.60(ABq, 4H); 1.85(m, 4H); 1.12(t, 6H). | 381 (M+.); 297; 84 EI; source 200 C; 70 V; 200 uA | 2980, 1730, 1600. |
| 11 | (DMSO): 7.30(dd, 1H); 7.25(d, 2H); 6.90(d, 2H); 6.71(m, 3H); 4.03(t, 2H); 3.75(s, 3H); 3.40–3.10(m, 10H); 1.88(m, 4H); 1.10(t, 6H). | 395 (M+.); 311; 211; 84 EI; source 200 C; 70 V; 200 uA | 2975, 1730, 1620. |
| 12 | (DMSO): 11.00(s br, 4H); 7.28(dd, 1H); 7.24(d, 2H); 7.90(d, 1H); 6.70(d, 1H); 6.70(d, 1H); 6.68(s, 1H); 3.93(t, 2H); 3.74(s, 3H); 3.34(d br, 4H); 2.91(t, 2H); 2.59(ABq, 4H); 2.52(s 6H); 1.10(t, 6H). | 369 (M+.); 311; 211; 58 EI; source 200 C; 70 V; 200 μA | 2980, 1620, 1600 (free base). |
| 13 | (DMSO): 11.00(s br, 4H); 9.34(s br, 1H); 7.62(d, 2H); 7.58(d, 2H); 7.42(dd, 2H); 7.30(dd, 1H); 7.14(dd, 1H); 6.71(d, 2H); 6.52(dd, 1H); 6.45(dd, 1H); 6.36(dd, 1H); 4.47(ddq, 1H); 2.80(m, 1H); 2.60(ABq, 4H); 2.55(s, 6H); 2.50(m, 1H); 1.12(d, 3H). | 346 (M+.); 288; 58 EI; source 200 C; 70 V; 200 μA | 3400, 1720, 1600. |
| 14 | (DMSO): 11.00(s br, 4H); 9.35(s br, 1H); 7.62(d, 2H); 7.59(d, 2H); 7.43(dd, 2H); 7.30(dd, 1H); 7.14(dd, 1H); 7.07(d, 2H); 6.55(dd, 1H); 6.49(d, 1H); 6.48(d, 1H); 4.01(dd, 1H); 3.75(dd, 1H); 3.33(m, 1H); 2.60(s, 6H); 2.58(ABq, 4H); 1.19(d, 3H). | 346 (M+.); 275; 274; 72 EI; source 200 C; 70 V; 200 μA | 3400, 1720, 1600. |
| 15 | (DMSO): 11.00(s br, 4H); 7.66(d, 2H); 7.60(d, 2H); 7.43(dd, 2H); 7.31(dd, 1H); 7.25(dd, 1H); 6.94(d, 2H); 6.67(dd, 1H); 6.53(dd, 1H); 6.51(s, 1H); 4.52(ddq, 1H); 3.70(s, 3H); 2.78(m, 1H); 2.60(ABq, 4H); 2.52(m, 1H); 2.51(s, 6H); 1.15(d, 3H). | 360 (M+.); 302; 58 EI; source 200 C; 70 V; 200 μA | 2985, 1600, 1490 (free base). |
| 16 | (DMSO): 11.00(s br, 4H); 7.63(d, 2H); 7.60(d, 2H); 7.43(dd, 2H); 7.31(dd, 1H); 7.24(dd, 1H); 7.09(d, 2H); 6.68–6.61(m, 3H); 4.02(dd, 1H); 3.79(dd, 1H); 3.72(s, 3H); 3.31(m, 1H); 2.59(s, 6H); 2.58(ABq, 4H); 1.18(d, 3H). | 360 (M+.); 289; 288; 72 EI; source 200 C; 70 V; 200 μA | 2985, 1600, 1490 (free base). |
| 17 | (DMSO, 353 K): 7.42–7.31(m, 5H); 7.00–6.92(m, 3H); 3.80(s, 3H); 3.40–3.30(m, 6H); 2.68(ABq, 4H); 2.42(s, 6H); 1.10(t, 6H). | 383 (M+.); 355; 325; 225; 58 EI; source 200 C; 70 V; 200 μA | 1730, 1690, 1600. |
| 18 | (DMSO): 11.00(s br, 4H); 7.40(d, 2H); 7.35(dd, 1H); 6.86(dd, 1H); 6.71–6.63(m, 4H); 4.51(m, 1H); 3.74(s, 3H); 3.43(m, 4H); 2.73(m, 1H); 2.62(ABq, 4H); 2.55(m, 1H); 2.50(s, 3H); 1.80(m, 4H); 1.11(d, 3H). | 381 (M+.); 323; 58 EI; source 200 C; 70 V; 200 μA | 2960, 1600, 1400 (free base). |
| 19 | (DMSO): 11.00(s br, 4H); 7.42(d, 2H); 7.31(dd, 1H); 6.89(d, 2H); 6.76(m, 3H); 4.01(dd, 1H); 3.81(dd, 1H); 3.74(s, 3H); 3.43(m, 4H); 3.38–3.22(m, 1H); 2.61(ABq, 4H); 2.60(s, 6H); 2.80(m, 4H); 1.15(d, 3H). | 381 (M+.); 310; 309; 72 EI; source 200 C; 70 V; 200 μA | 2960, 1600, 1400 (free base). |
| 20 | (DMSO): 10.80(s br, 4H); 9.50(s br, 1H); 7.39(d, 2H); 7.23(dd, 1H); 6.69(dd, 1H); 6.68(d, 2H); 6.55(dd, 1H); 6.49(d, 1H); 4.50(ddq, 1H); 3.40(m, 4H); 2.75(m, 1H); 2.60(ABq, 4H); 2.55(m, 1H); 1.83(m, 4H); 1.10(d, 3H). | 367 (M+.); 309; 58 EI; source 200 C; 70 V; 200 μA | 2960, 1600, 1430 (free base). |
| 21 | (CDCl3): 7.33(d, 2H); 7.04(dd, 1H); 6.81(d, 2H); 6.66(dd, 1H); 6.54(dd, 1H); 6.44(dd, 1H); 4.20(dd, 1H); 3.65(dd, 1H); 3.55–3.35(m, 5H); 2.72(ABq, 4H); 1.90–1.75(m, 4H); 1.25(m, 3H). | 367 (M+.); 296; 295; 72 EI; source 200 C; 70 V; 200 μA | 2960, 1600, 1440 (free base). |
| 22 | (DMSO): 10.80(s br, 4H); 9.40(s br, 1H); 7.30(dd, 1H); 7.14(dd, 1H); 6.92(dd, 1H); 6.85(d, 1H); 6.65(s br, 1H); 6.55(dd, 1H); 6.44(dd, 1H); 4.46(ddq, 1H); 3.40–3.10(m, 4H); 2.75(dd, 1H); 2.61(ABq, 4H); 2.60(s, 6H); 1.10(d, 3H); 1.00(t, 6H). | 369 (M+.); 311; 58 EI; source 200 C; 70 V; 200 μA | 3420, 1730, 1590. |
| 23 | (DMSO): 10.90(s br, 4H); 9.40(s br, 1H); 7.33(dd, 1H); 7.13(dd, 1H); 7.06(dd, 1H); 6.88(d, 1H); 6.81(s, 1H); 6.54(dd, 1H); 6.50(dd, 1H); 6.45(s br, 1H); 3.99(dd, 1H); 3.74(dd, 1H); 3.40–3.10(m, 5H); 2.61(s, 6H); 2.60(ABq, 4H); 1.18(d, 3H); 1.15–0.90(m, 6H). | 369 (M+.); 298; 72 EI; source 200 C; 70 V; 200 uA | 3420, 1730, 1590. |
| 24 | (DMSO): 10.85(s br, 4H); 9.42(s br, 1H); 7.20(dd, 1H); 7.14(d, 2H); 6.71(d, 2H); 6.64(dd, 1H); 6.50(dd, 1H); 6.44(dd, 1H); 4.46(ddq, 1H); 3.70(m, 2H); 2.73(dd, 1H); 2.61(ABq, 4H); 2.51(dd, 1H); 2.51(s, 6H); 1.26(d, 12H); 1.13(d, 3H). | 397 (M+.); 339; 297; 211; 58 EI; source 200 C; 70 V; 200 uA | 2960, 1735, 1595. |
| 25 | (DMSO): 10.95(s br, 4H); 9.45(s br, 1H); 7.17(d, 2H); 7.16(dd, 1H); 6.90(d, 1H); 6.60(dd, 1H); 6.55(d, 1H); 6.53(s br, 1H); 3.96(dd, 1H); 3.80–3.65(m, 3H); 3.35–3.20(m, 2H); 2.59(ABq, 4H); 2.57(s, 6H); 1.27(d, 12H); 1.15(d, 3H). | 397 (M+.); 325; 197; 72 EI; source 200 C; 70 V; 200 uA | 2960, 1735, 1595. |
| 26 | (DMSO): 10.90(s br, 4H); 9.40(s br, 1H); 7.32(dd, 1H); 7.16(dd, 1H); 6.93(dd, 1H); 6.87(d, 1H); 6.67(s br, 1H); 6.55(dd, 1H); 6.44(dd, 1H); 6.35(dd, 1H); 4.48(ddq, 1H); 3.50–2.80(m, 10H); 2.60(ABq, 4H); 1.85(m, 4H); 1.15(d, 3H); 1.05(m, 6H). | 395 (M+.); 311; 84 EI; source 200 C; 70 V; 200 uA | 2970, 1595, 1450 (free base). |

TABLE 5-continued

| Ex. | NMR | MS | IR cm$^{-1}$ (KBr) |
|---|---|---|---|
| 27 | (DMSO): 11.00(s br, 4H); 9.40(s br, 1H); 7.33(dd, 1H); 7.14(dd, 1H); 7.06(dd, 1H); 6.88(d, 1H); 6.83(s br, 1H); 6.54(d, 1H); 6.48(d, 1H); 6.46(s br, 1H); 4.09(dd, 1H); 3.76(dd, 1H); 3.50–3.00(m, 9H); 2.60(ABq, 4H); 1.85(m, 4H); 1.22(d, 3H); 1.00(m, 6H). | 395 (M+.); 298, 297, 98 EI; source 200 C; 70 V; 200 uA | 2970, 1595, 1450 |
| 28 | (DMSO): 10.08(s br, 1H); 9.55(s br, 1H); 7.23(d, 2H); 7.22(dd, 1H); 6.85(d, 2H); 6.66(dd, 1H); 6.60(dd, 1H); 6.54(dd, 1H); 4.55(dddd, 1H); 3.70–3.40(m, 6H); 3.40–3.25(m, 4H); 2.10–1.90(m, 4H); 1.75–1.50(m, 2H); 1.10(t, 6H); 0.99(t, 3H). | 409 (M+.); 325; 84 EI; source 200 C; 70 V; 200 uA | 3410, 2970, 1600. |
| 29 | (DMSO): 10.40(s br, 1H); 9.52(s br, 1H); 7.26(d, 2H); 7.19(dd, 1H); 6.95(d, 2H); 6.64(dd, 1H); 6.58(dd, 1H); 6.56(d, 1H); 4.13(dd, 1H); 3.99(dd, 1H); 3.68–3.56(m, 1H); 3.54–3.41(m, 1H); 3.40–3.25(m, 5H); 3.25–3.10(m, 2H); 2.05–1.70(m, 6H); 1.10(t, 6H); 0.91(t, 3H). | 409 (M+.); 297; 197; 112 EI; source 180 C; 70 V; 200 uA | 3180, 2970, 1600. |
| 30 | (CDCl3): 7.35(m, 3H); 6.75–6.55(m, 5H); 4.3(m, 1H); 3.8(s, 3H); 3.4(m, 4H); 2.5–2.4(m, 1H); 2.35(s, 6H); 2.1(m, 1H); 1.2(t, 9H). | 383 (M+.); 325 EI; source 200 C; 70 V; 200 uA | 2970, 1620, 1595. |
| 31 | (CDCl3): 7.30–7.20(m, 3H); 6.90(m, 2H); 6.70–6.55(m, 3H); 3.85(m, 1H); 3.8(s, 3H); 3.75–3.45(m, 5H); 2.95(m, 1H); 2.25(s, 6H); 1.2(t, 6H); 1.0(d, 3H). | 383 (M+.); 312 EI; source 200 C; 70 V; 200 uA | 2970, 1620, 1595. |
| 32 | — | — | 2980, 1635, 1595. |
| 33 | — | — | 2980, 1635, 1595. |
| 34 | — | — | 2990, 1630, 1600. |
| 35 | — | — | 2990, 1630, 1600. |
| 36 | — | — | 2960, 1630, 1580. |
| 37 | — | — | 2960, 1630, 1580. |
| 38 | (DMSO): 10.2(s br, 1H); 7.40–7.20(m, 3H); 6.90–6.70(m, 5H); 4.55(dddd, 1H); 3.85(s, 3H); 3.80–3.30(m, 9H); 2.10–1.60(m, 7H); 1.10(t, 6H); 0.95(t, 3H). | 423 (M+.); 339; 84. EI; source 200 C; 70 V; 200 uA | 2980, 1600, 1490. |
| 39 | (DMSO): 10.70(s br, 1H); 7.27(m, 3H); 7.05(m, 2H); 6.7(m, 3H); 4.50–4.00(m, 6H); 3.85(s, 3H); 3.80–3.30(m, 9H); 2.00–1.70(m, 2H); 1.10(t, 6H); 0.91(t, 3H). | 423 (M+.); 311; 211; 112. EI; source 200 C; 70 V; 200 uA | 2980, 1600, 1490. |
| 40 | (DMSO): 10.20(s br, 1H); 9.50(s, 1H); 7.24(d, 2H); 7.22(dd, 1H); 6.80(m, 2H); 6.69(d, 1H); 6.56(dd, 1H); 6.49(s, 1H); 6.04–5.86(m, 1H); 5.47(m, 2H); 4.80–4.68(m, 1H); 3.90–3.70(m, 2H); 3.31(q br, 4H); 3.25–3.01(m, 2H); 2.82(s br, 3H); 1.23(d, 3H); 1.12(t, 6H). | 395 (M+.); 311; 211; 84 EI; source 180 C; 70 V; 200 uA | 3410, 2970, 1600. |
| 41 | (DMSO): 10.22 and 10.10(s br, 1H); 9.50(s, 1H); 7.25(d, 2H); 7.19(dd, 1H); 6.99–6.92(m, 2H); 6.64(dd, 1H); 6.58(d, 1H); 6.55(s, 1H); 5.98–5.82(m, 1H); 5.55–5.38(m, 2H); 4.20(dd, 1H); 4.00–3.77(m, 2H); 3.75–3.63(m, 1H); 3.60–3.50(m, 1H); 3.32(q br, 4H); 2.73 and 2.70(d, 3H); 1.35 and 1.27(d, 3H); 1.10(t, 3H). | 395 (M+.); 298; 297; 197; 98 EI; sorgente 180 C; 70 V; 200 uA | 3180, 2970, 1600. |
| 42 | (DMSO- 353K): 10.05(s br, 1H); 9.72(s br, 1H); 7.44(ABq, 1H); 7.41(ABq, 1H); 7.28(dd, 1H); 6.90(d br, 1H); 6.87–6.83(m, 2H); 4.05(s, 2H); 3.35(q, 4H); 2.87(s, 6H); 1.11(t, 3H). | 370 (MH+.) CI; gas reagente isobutano; P 4000 m Torr; sorgente 150 C; | 3400, 1680, 1605. |
| 43 | (CDCl3): 7.49(d, 2H); 7.11(s br, 1H); 7.07(dd, 1H); 7.02(d, 2H); 6.36(d, 1H); 6.29(d, 1H); 6.28(s, 1H); 4.30–4.20(m, 1H); 3.72(s, 3H); 2.61–2.46(m, 6H); 2.35(dd, 1H); 1.75(m, 4H); 1.23(d, 6H); 1.19(d, 3H). | 395 (M+.); 312; 311; 84 EI; TSQ 700; sorgente 180 C; 70 V; 200 μA | 3280, 2960, 1660. |
| 44 | (DMSO): 9.85(s, 1H); 9.05(s br, 1H); 7.64(d, 2H); 7.00(d, 2H); 6.95(d, 1H); 6.18(m, 2H); 6.02(dd, 1H); 4.38(dt, 1H); 3.15–2.80(m, 6H); 2.62(ABq, 1H); 2.59(m, 1H); 2.54(ABq, 1H); 1.86(m, 4H); 1.12(d, 3H); 1.11(d, 6H). | 381 (M+.); 297; 84 EI; TSQ 700; sorgente 180 C; 70 V; 200 μA | 3300, 2960, 1670. |
| 45 | (CDCl3 + TFA): 9.10(s br, 1H); 7.30(dd, 1H); 7.26(d, 2H); 6.90(d, 1H); 6.80(d, 2H); 6.78(s, 1H); 6.62(d, 1H); 4.68(m, 1H); 3.71–3.45(m br, 4H); 3.33(m, 1H); 3.10(m, 1H); 3.00(d, 6H); 1.32(m, 9H). | 369 (M+.); 311 EI; TSQ 700; sorgente 180 C; 70 V; 200 μA | |
| 46 | (CDCl3 + TFA): 9.10(s br, 1H); 7.30(dd, 1H); 7.26(d, 2H); 6.90(d, 1H); 6.80(d, 2H); 6.62(s, 1H); 6.62(d, 1H); 4.68(m, 1H); 3.71–3.45(m br, 4H); 3.33(m, 1H); 3.10(m, 1H); 3.00(d, 6H); 1.32(m, 9H). | 369 (M+.); 311 EI; TSQ 700; sorgente 180 C; 70 V; 200 μA | |
| 47 | (DMSO): 10.05(s br, 1H); 9.51(s br, 1H); 7.70–7.13(m, 5H); 7.05–6.70(m 3H); 3.95(s, 2H); 3.49–3.14(m, 8H); 1.20(t, 6H); 1.10(s br, 6H). | 398 (M+.); 86 CI; gas reagente isobutano; P 4000 m Torr; sorgente 150 C; | 3400, 1680, 1600. |
| 48 | (DMSO): 10.19(s br, 1H); 10.01(s br, 1H); 7.60–7.20(m, 5H); 7.00–6.70(m, 3H); 4.11(s, 1H); 3.60–3.00(m, 8H); 1.90(m, 4H); 1.10(t, 6H). | 396 (M+.); 84 CI; gas reagente isobutano; P 4000 m Torr; sorgente 150 C; | 3450, 1675, 1605. |
| 49 | (CDCl3): 7.27(s, 4H); 7.15(dd, 1H); 6.73(m, 2H); 6.66(d, 1H); 3.75(m br, 2H); 3.10(s, 3H); 2.32(s, 6H); 1.35(m br, 12H); | 397 (M+.); 369; 58 EI; TSQ 700; sorgente 180 C; 70 V; 200 μA | 3400, 1680, 1600. |
| 50 | (CDCl3 - as a base): 7.36(d, 2H); 7.28(d, 2H); 7.20(dd, 1H); 6.77(d, 1H); 6.72(m, 2H); 5.86–5.73(m, 1H); 5.21–5.12(m, 2H); 3.61–3.45(m br, 2H); 3.45–3.26(m br, 2H); 3.20(s, 2H); 3.15(d, 2H); 2.37(s, 3H); 1.20(m br, 6H). | 395 (M+.); 325; 84; 41 EI; TSQ 700; sorgente 180 C; 70 V; 200 μA | 3400, 1675, 1600. |
| 51 | (CDCl3): 7.40(m, 4H); 7.30(dd, 1H); 6.84(d, 1H); 6.73(d, 1H); 6.72(s, 1H); 3.70–3.10(m, 6H); 3.40(s, 2H); 2.51(s, 3H); 1.30(s br, 6H). | 355 (M+.); 284; 212 EI; TSQ 700; sorgente 180 C; 70 V; 200 μA | 3450, 1680, 1610. |
| 52 | (CDCl3 + TFA): 7.48(s br, 5H); 7.35(m, 5H); 7.00(d, 1H); 6.88(d, 1H); 6.80(s, 1H); 3.91(s br, 2H); 3.75(m, 2H); 1.55(d, 3H); 1.22(d, 3H). | 369 (M+.); 312; 269; 212 EI; TSQ 700; sorgente 180 C; 70 V; 200 μA | 3400, 1675, 1600. |
| 53 | — | — | 2990, 1630, 1600. |
| 54 | — | — | 2980, 1630, 1590. |
| 55 | — | — | 2990, 1680, 1590. |
| 56 | — | — | 2990, 1675, 1600. |
| 57 | — | — | 2980, 1675, 1600. |
| 58 | — | — | 2990, 1680, 1600. |
| 59 | — | — | 2990, 1675, 1595. |
| 60 | — | — | 3000, 1680, 1600. |
| 61 | — | — | 3370, 2960, 1610. |

We claim:
1. A compound, or solvate or salt thereof, of formula (I)

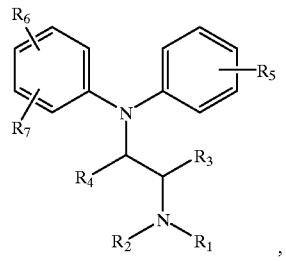

in which,
R$_1$ and R$_2$, are, independently hydrogen, linear or branched C$_{1-6}$ alkyl, C$_{3-7}$ cycloalkyl, C$_{3-7}$ cycloalkenyl, or C$_{3-6}$ alkenyl, or together form a C$_{3-7}$ alkyl ring;
R$_3$ and R$_4$ are, independently, hydrogen, linear or branched C$_{1-6}$ alkyl, or R$_4$ is oxygen forming with the carbon atom to which is attached a C=O group;
R$_5$ is hydrogen, hydroxy, or C$_{1-3}$ alkoxy;
R$_6$ is halogen, NH$_2$ or a para or meta —COR-8 group, in which R$_8$ is C$_{1-8}$-alkyl, C$_{1-8}$-alkoxy or NR$_9$R$_{10}$, wherein R$_9$ and R$_{10}$, are, independently hydrogen, straight or branched C$_{1-6}$ alkyl, C$_{3-7}$ cycloalkyl or phenyl;
or R$_6$ is a para or meta

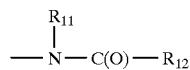

group
in which R$_{11}$ and R$_{12}$ are, independently, hydrogen or straight or branched C$_{1-6}$ alkyl and,
R$_7$ is hydrogen, or straight or branched C$_{1-8}$ alkyl.

2. A compound according to claim 1 in which each of R$_1$ and R$_2$ is methyl, ethyl, cyclopropylmethyl, allyl, or together with the N atom, pyrrolidino.

3. A compound according to claim 1, in which each of R$_3$ and R$_4$ is hydrogen, methyl, ethyl, iso-propyl or R4 is oxo.

4. A compound according to claim 1 in which R$_5$ is hydrogen, hydroxy or methoxy.

5. A compound according to claim 1 in which R$_6$ is COMe, CO—i—Pr, COOEt, CONH$_2$, CONH—n—Pr, CON(Me)Et, CON(Me)i—Pr, CONEt$_2$, CON(—Pr)$_2$, CONEt(i—Pr), CON(—CH$_2$—)$_4$, NHCOi—Pr, NH$_2$, bromine or phenyl.

6. A compound according to of claim 1 in which R$_7$ is hydrogen methyl.

7. A compound selected from:
(−)-3-[N-(3-pyrrolidinoprop-2-yl) phenylamino]-N-propylbenzamide;
(±)-N-(4-bromophenyl)-N-(3-hydroxyphenyl)-α-methyl-1-pyrrolidinoethanamine;
(±)-N-(4-bromophenyl)-N-(3-methoxyphenyl)-α-methyl-1-pyrrolidinoetanamine;
(±)-N,N-(4)-N,N-diethyl-4-[[N-(3-methoxyphenyl)-N-(3-pyrrolidinoprop-2-yl)]amino]benzamide;
(±)-N,N-diethyl-4-[[N-(3-hydroxyphenyl)-N-(3-pyrrolidinoprop-2-yl)]amino]benzamide;
N-(4-bromophenyl)-N-(3-hydroxyphenyl)-1-pyrrolidinoethanamine;
N,N-diethyl-4-[[N-(2-dimethylaminoethyl)-N-(3-hydroxyphenyl)]amino]benzamide;
(±)-N,N-diethyl-4-[[N-(2-dimethylaminoprop-1-yl)-N-(3-hydroxyphenyl)]amino]benzamide;
(±)-N,N-diethyl-4-[[N-(3-dimethylaminoprop-2-yl)-N-(3-hydroxyphenyl)]amino]benzamide;
N,N-diethyl-4-[[N-(3-hydroxyphenyl)-N-(2-pyrrolidinoethyl)]amino]benzamide;
N,N-diethyl-4-[[N-(3-methoxyphenyl)-N-(2-pyrrolidinoethyl)]amino]benzamide;
N,N-diethyl-4-[[N-(2-dimethylaminoethyl)-N-(3-methoxyphenyl)]amino]benzamide;
N,N-diethyl-4-[[N-(2-dimethylaminoethyl)-N-(3-methoxyphenyl)]amino]benzamide;
(±)-N$^2$-(4-biphenylyl)-N$^1$,N$^1$-dimethyl-N$^2$-(3-hydroxyphenyl)-1,2-propandiamine;
(±)-N$^1$-(4-biphenylyl)-N$^2$,N$^2$-dimethyl-N$^1$-(3-hydroxyphenyl)-1,2-propandiamine;
(±)-N$^2$-(4-biphenylyl)-N$^1$,N$^1$-dimethyl-N$^2$-(3-methoxyphenyl)-1,2-propandiamine;
(±)-N$^1$-(4-biphenylyl)-N$^2$,N$^2$-dimethyl-N$^1$-(3-methoxyphenyl)-1,2-propandiamine;
N,N-diethyl-4-[[N-(dimethylaminoacetyl)-N-(3-methoxyphenyl)]amino]benzamide;
(±)-1-[4-[[N-(3-dimethylaminoprop-2-yl)-N-(3-methoxyphenyl)]amino]benzoyl]pyrrolidine;
(±)-1-[4-[[N-(2-dimethylaminoprop-1-yl)-N-(3-methoxyphenyl)]amino]benzoyl]pyrrolidine;
(±)-1-[4-[[N-(3-dimethylaminoprop-2-yl)-N-(3-hydroxyphenyl)]amino]benzoyl]pyrrolidine;
(±)-1-[4-[[N-(2-dimethylaminoprop-1-yl)-N-(3-hydroxyphenyl)]amino]benzoyl]pyrrolidina;
(±)-N,N-diethyl-3-[[N-(3-dimethylaminoprop-2-yl)-N-(3-hydroxyphenyl)]amino]benzamide;
(±)-N,N-diethyl-3-[[N-(2-dimethylaminoprop-1-yl)-N-(3-hydroxyphenyl)]amino]benzamide;
(±)-N,N-diisopropyl-4-[[N-(3-dimethylaminoprop-2-yl)-N-(3-hydroxyphenyl)]amino]benzamide;
(±)-N,N-diisopropyl-4-[[N-(2-dimethylaminoprop-1-yl)-N-(3-hydroxyphenyl)]amino]benzamide;
(±)-N,N-diethyl-3-[[N-(3-hydroxyphenyl)-N-(3-pyrrolidinoprop-2-yl)]amino]benzamide;
(±)-N,N-diethyl-3-[[N-(3-hydroxyphenyl)-N-(2-pyrrolidinoprop-1-yl)] amino]benzamide;
(±)-N,N-diethyl-4-[[N-(3-hydroxyphenyl)-N-(1-pyrrolidinyl-2-butyl) amino]benzamide;
(±)-N,N-diethyl-4-[[N-(3-hydroxyphenyl)-N-(2-pyrrolidinyl-1-butyl)]amino]benzamide;
(±)-N,N-diethyl[[N-(2-dimethylaminoprop-1-yl)-N-(3-methoxyphenyl)]amino]benzamide;
(±)-N,N-diethyl-4-[[N-(3-dimethylaminoprop-2-yl)-N-(3-methoxyphenyl)]amino]benzamide;
(±)-N,N-diethyl-3-[[N-(3-dimethylaminoprop-2-yl)-N-(3-methoxyphenyl)]amino]benzamide;
(±)-N,N-diethyl-3-[[N-(2-dimethylaminoprop-1-yl)-N-(3-methoxyphenyl)]amino]benzamide;
(±)-N,N-diisopropyl-4-[[N-(3-dimethylaminoprop-2-yl)-N-(3-methoxyphenyl)]amino]benzamide;
(±)-N,N-diisopropyl-4-[[N-(2-dimethylaminoprop-1-yl)-N-(3-methoxyphenyl)]amino]benzamide;

(±)-N,N-diethyl-3-[[N-(3-methoxyphenyl)-N-(3-pyrrolidinoprop-2-yl)]amino]benzamide;

(±)-N,N-diethyl-3-[[N-(3-methoxyphenyl)-N-(2-pyrrolidinoprop-1-yl)]amino]benzamide;

(±)-N,N-diethyl[[N-(3-methoxyphenyl)-N-(1-pyrrolidinyl-2-butyl)]amino]benzamide;

(±)-N,N-diethyl-4-[[N-(3-methoxyphenyl)-N-(2-pyrrolidinyl-1-butyl)]amino]benzamide;

(±) 4-[N-[1-(N-allyl-N-methyl)amino-2-propyl]-N-(3-hydroxyphenyl)amino]-N, N-diethylbenzamide;

(±)-4-[N-[2-(N-allyl-N-methyl)amino-1-propyl]-N-(3-hydroxyphenyl)amino]-N, N-diethylbenzamide;

N,N-diethyl-4[[N-(dimethylaminoacetyl)-N-(3-hydroxyphenyl)]amino]benzamide;

(±)-N-[[4-[N-(3-methoxyphenyl)-N-[1-methyl-2-(1-pyrrolidinyl) ethyl]]amino]phenyl]-2-methylpropanamide;

(±)-N-[[4-[N-(3-hydroxyphenyl)-N-[1-methyl-2-(1-pyrrolidinyl) ethyl]]amino]phenyl]-2-methylpropanamide;

(−)-N,N-diethyl-4-[[N-(3-dimethylaminoprop-2-yl)N-(3-; hydroxyphenyl)]amino]benzamide;

(+)-N,N-diethyl-4-[[N-(3-dimethylaminoprop-2-yl)-N-(3-hydroxyphenyl)]amino]benzamide;

N,N-diethyl-4-[[N-(diethylaminoacetyl)-N-(3-hydroxyphenyl)]amino]benzamide;

N,N-diethyl-4-[[N-(3-hydroxyphenyl)-N-(pyrrolidin-1-ylacetyl)]amino]benzamide;

N,N-diisopropyl-4[[N-(dimethylaminoacetyl)-N-(3-hydroxyphenyl)]amino]benzamide;

4-[[N-[[(N-allyl-N-methyl)amino]acetyl-N-(3-hydroxyphenyl)]amino]-N,N-diethylbenzamide;

N,N-diethyl-4-[[N-(3-hydroxyphenyl)-N-(methylaminoacetyl)]amino]benzamide;

N,N-diisopropyl-4-[[N-aminoacetyl-N-(3-hydroxyphenyl)]amino]benzamide;

(±)-4(N-[1-(N-allyl-N-methyl)amino-2-propyl]-N-(3-methoxyphenyl)amino]-N,N,-diethylbenzamide;

(±)-4-[N-[2-(N-allyl-N-methyl)amino-1-propyl]-N-(3-methoxyphenyl)amino]-N,N-diethylbenzamide;

N,N-diethyl-4-[[N-(diethylaminoacetyl)-N-(3-methoxyphenyl)]amino]benzamide;

N,N-diethyl-4-[[N-(3-methoxyphenyl)-N-(pyrrolidin-1-ylacetyl)]amino]benzamide;

N,N-diisopropyl-4-[[N-(dimethylaminoacetyl)-N-(3-methoxyphenyl)]amino]benzamide;

4-[[N-[[(N-allyl-N-methyl)amino]acetyl]-N-(3-methoxyphenyl)]amino]-N,N-diethylbenzamide;

N,N-diethyl-4-[[N-(3-methoxyphenyl)-N-(methylaminoacetyl)]amino]benzamide;

N,N-diisopropyl-4-[[N-aminoacetyl-N-(3-methoxyphenyl)]amino]benzamide;

(±)-N-(4-aminophenyl)-N-(3-methoxyphenyl)-α-methyl-1-pyrrolidinoetanamine.

8. A pharmaceutical composition comprising a compound according to claim 1 and a pharmaceutically acceptable carrier.

9. A method for treating diseases mediated by the delta receptor which comprises administering an effective amount of a compound according to claim 1.

10. A method for the treatment or prophylaxis of pain, rejection of organ transplant or skin grafts, allergy, inflammation, drug or alcohol abuse, diarrhea, cardiovascular or respiratory diseases, cough, mental illness, epilyetic seizures or other neurological diseases, or for protecting brain cells, or for decreasing gastric secretion, which comprises administering a compound according to claim 9.

* * * * *